US010330958B2

United States Patent
Fonte et al.

(10) Patent No.: US 10,330,958 B2
(45) Date of Patent: Jun. 25, 2019

(54) SYSTEMS AND METHODS FOR CREATING EYEWEAR WITH MULTI-FOCAL LENSES

(71) Applicant: BESPOKE, INC., San Francisco, CA (US)

(72) Inventors: Timothy A. Fonte, San Francisco, CA (US); Eric J. Varady, San Francisco, CA (US)

(73) Assignee: Bespoke, Inc., San Francisco, CA (US)

( * ) Notice: Subject to any disclaimer, the term of this patent is extended or adjusted under 35 U.S.C. 154(b) by 22 days.

(21) Appl. No.: 15/095,031

(22) Filed: Apr. 9, 2016

(65) Prior Publication Data

US 2016/0299360 A1    Oct. 13, 2016

Related U.S. Application Data

(60) Provisional application No. 62/145,862, filed on Apr. 10, 2015.

(51) Int. Cl.
*A61B 3/11* (2006.01)
*G02C 7/02* (2006.01)
(Continued)

(52) U.S. Cl.
CPC ............ *G02C 13/005* (2013.01); *A61B 3/111* (2013.01); *G02C 7/027* (2013.01); *G02C 7/028* (2013.01);
(Continued)

(58) Field of Classification Search
CPC .... G02C 7/025; G02C 13/003; G02C 13/005; G02C 7/027; G02C 7/028; A61B 3/111;
(Continued)

(56) References Cited

U.S. PATENT DOCUMENTS 6,095,650 A * 8/2000 Gao ..................... G02C 13/005
                                                351/227
6,142,628 A * 11/2000 Saigo ................... G02C 13/003
                                                351/204

(Continued)

FOREIGN PATENT DOCUMENTS

FR          3 006 776 A1    12/2014
WO      WO 01/88654 A2      11/2001
WO      WO 2014/046206 A1    3/2014

OTHER PUBLICATIONS

International Search Report and Written Opinion for corresponding Application No. PCT/US2016/026837 dated Aug. 5, 2016 (13 pages).

*Primary Examiner* — Rehana Perveen
*Assistant Examiner* — Justin C Mikowski
(74) *Attorney, Agent, or Firm* — Bookoff McAndrews, PLLC

(57) ABSTRACT

Systems and methods are disclosed for generating an eyewear frame and lens geometry that is customized to a user's anatomy and optimized for optical performance. One method includes receiving a configurable parametric model of a user-specific eyewear product comprising a frame portion and a lens portion, wherein geometric parameters of the configurable parametric model are based geometric features of a user's anatomy; receiving media data of a user, the media data including the user's response to visual cues; detecting the position of the user's eyes from the received media data; determining optical information of the user based on the detected position of the user's eyes; and generating an updated configurable parametric model by modifying the received configurable parametric model based on the determined optical information.

20 Claims, 10 Drawing Sheets

(51) Int. Cl.
  *G06F 3/01* (2006.01)
  *G02C 13/00* (2006.01)
  *G06F 17/50* (2006.01)
  *G06Q 30/06* (2012.01)
  *G06T 15/10* (2011.01)
  *G06T 17/00* (2006.01)
  *G06T 19/20* (2011.01)

(52) U.S. Cl.
  CPC .............. *G06F 3/013* (2013.01); *G06F 17/50* (2013.01); *G06Q 30/0621* (2013.01); *G06T 15/10* (2013.01); *G06T 17/00* (2013.01); *G06T 19/20* (2013.01); *G06T 2219/2004* (2013.01)

(58) Field of Classification Search
  CPC ..... G06F 3/013; G06F 17/50; G06Q 30/0621; G06T 15/10; G06T 17/00; G06T 19/20; G06T 2219/2004
  USPC .......................................................... 703/1
  See application file for complete search history.

(56) References Cited

U.S. PATENT DOCUMENTS

| | | | | |
|---|---|---|---|---|
| 6,286,957 B1 * | 9/2001 | Livnat | .................. | G02C 13/005 351/204 |
| 6,692,127 B2 * | 2/2004 | Abitbol | .............. | G06Q 30/0641 345/419 |
| 6,944,327 B1 * | 9/2005 | Soatto | .................. | G02C 13/003 351/159.75 |
| 7,006,956 B1 * | 2/2006 | Gerlovin | ............. | G06F 17/5009 703/6 |
| 7,287,853 B2 * | 10/2007 | Toshima | .................. | A61B 3/10 351/205 |
| 8,082,188 B2 * | 12/2011 | Shinohara | .......... | G06Q 30/0603 351/158 |
| 8,090,628 B2 * | 1/2012 | Shinohara | ............ | G02C 13/003 351/200 |
| 8,118,427 B2 * | 2/2012 | Bonnin | .............. | G02B 27/0172 351/159.75 |
| 8,876,287 B2 * | 11/2014 | Back | ...................... | G02C 7/041 351/159.1 |
| 9,086,582 B1 * | 7/2015 | Barton | ................. | G02C 13/005 |
| 9,230,062 B2 * | 1/2016 | Seriani | ............... | G06F 19/3418 |
| 9,245,499 B1 | 1/2016 | Surkov et al. | | |
| 9,341,867 B1 * | 5/2016 | Kim | ...................... | G02C 13/005 |
| 2003/0081173 A1 * | 5/2003 | Dreher | ................ | G02C 13/003 351/204 |
| 2004/0189935 A1 | 9/2004 | Warden et al. | | |
| 2012/0109589 A1 * | 5/2012 | Thompson | .......... | G06F 17/5086 703/1 |
| 2012/0109591 A1 * | 5/2012 | Thompson | .............. | G06F 17/50 703/1 |
| 2013/0141468 A1 * | 6/2013 | Coon | ....................... | G09G 5/00 345/661 |
| 2014/0253875 A1 * | 9/2014 | Le Gallou | ........... | G02C 13/005 351/204 |
| 2015/0032242 A1 * | 1/2015 | Schouwenburg | ... | B29C 67/0088 700/98 |
| 2015/0049304 A1 * | 2/2015 | Cussac | .................. | G02C 7/028 351/159.75 |
| 2015/0055086 A1 | 2/2015 | Fonte et al. | | |
| 2015/0077704 A1 * | 3/2015 | Carmon | ................. | A61B 3/028 351/159.74 |
| 2015/0146168 A1 * | 5/2015 | Divo | .................... | A61B 3/0091 351/204 |
| 2015/0293382 A1 * | 10/2015 | Jethmalani | .......... | G02C 13/005 351/204 |
| 2015/0339511 A1 * | 11/2015 | Thomet | .................. | A61B 5/103 348/78 |
| 2016/0103335 A1 * | 4/2016 | Ben-Shahar | ........ | G02C 1/00 351/158 |
| 2016/0124249 A1 * | 5/2016 | Haddadi | ................ | A61B 3/111 351/204 |
| 2016/0287069 A1 * | 10/2016 | Haddadi | ................ | A61B 3/113 |
| 2016/0327815 A1 * | 11/2016 | Rego | .................... | G02C 13/003 |
| 2016/0342206 A1 * | 11/2016 | Shazly | .................. | A61B 5/1114 |

* cited by examiner

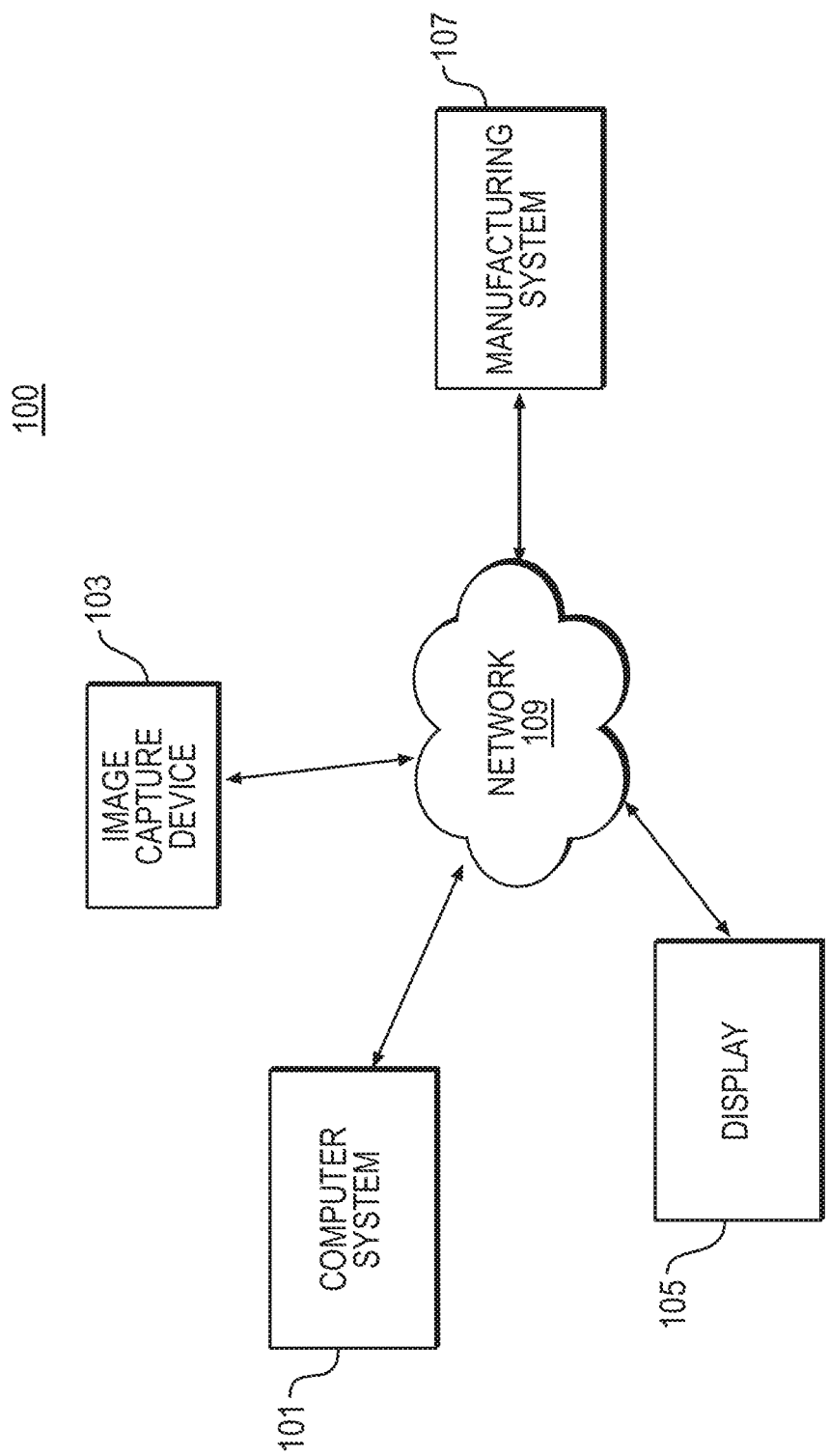

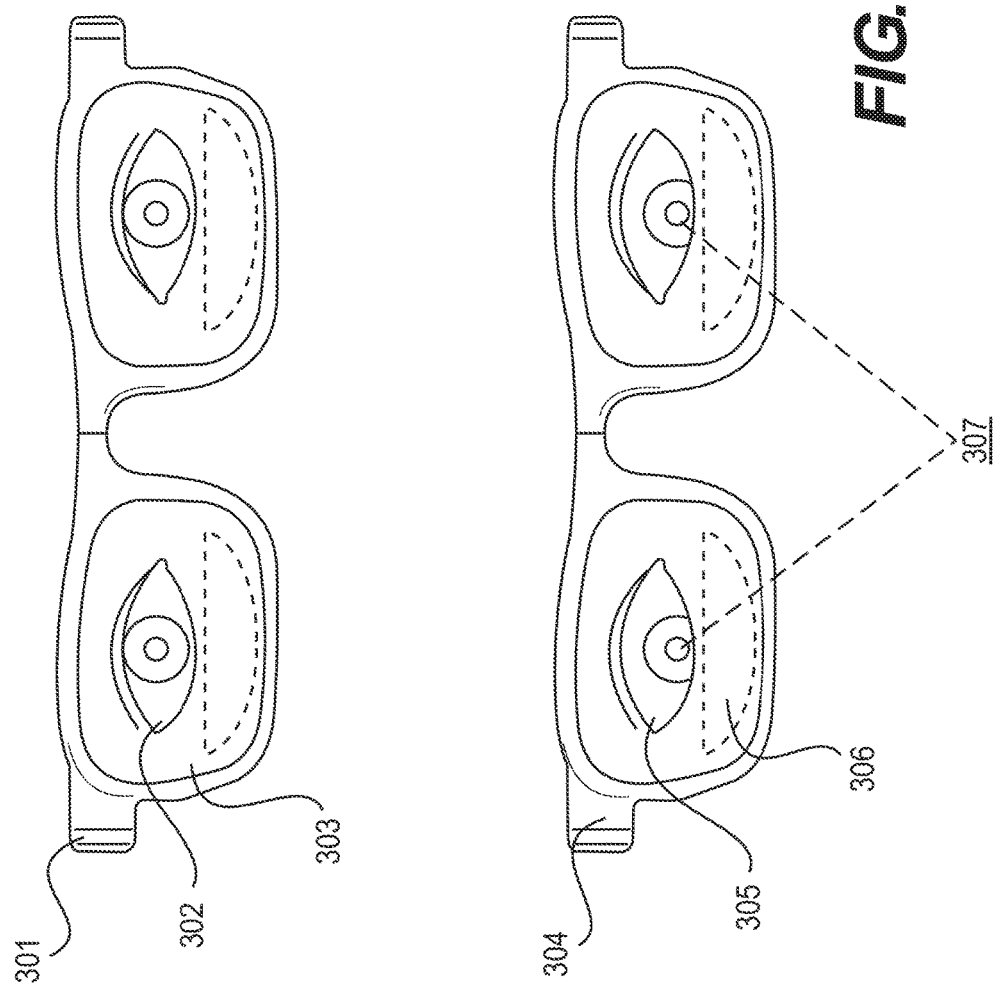

SYSTEMS AND METHODS FOR CREATING EYEWEAR WITH MULTI-FOCAL LENSES

RELATED APPLICATIONS

This application claims priority to U.S. Provisional Application No. 62/145,862 filed Apr. 10, 2015, the entire disclosure of which is hereby incorporated by reference in its entirety.

FIELD OF DISCLOSURE

Various embodiments of the present disclosure relate generally to creating, manufacturing, and delivering products customized to a user's specific anatomy and posture.

BACKGROUND

Many personal products exist that one might want to have customized or made as a one-of-a kind product tailored to a particular user. One such personal product may include eyewear. Purchasing eyewear, while a necessity for many people, presents many challenges for consumers. For traditional in-store purchases, consumers are faced with limited in-store selection, which often requires visiting multiple stores. Yet users must explore a burdensome array of options to find a compromise between fit, style, color, shape, price, etc. Eyewear is most commonly mass-produced, with a particular style available in one or two generic colors and sizes. Users' faces are unique enough that a face can be used as a primary form of identification, yet they must choose between products made for a generic faces that are not their own. It is very difficult for users to find the one perfect pair of glasses for their unique taste, facial anatomy, and needs. They also often have difficulty visualizing what they try on because they need an optical prescription in the first place.

Thus, there is a compelling need for methods and systems to allow greater and more personalized customization of eyewear lenses and frames, more accurate modeling and preview, more automated or assisted eyewear selection and customization, more detailed measurements, and improved methods to produce customized eyewear efficiently and economically to fulfill users' orders. In particular, ordering and creating advanced multi-focal optics, e.g., bifocals, trifocals, progressive, or digitally compensated lenses, may involve more information and as compared to standard single-vision optics in order to achieve desired benefits. These types of eyewear may be difficult to order remotely or without excessive equipment, time, and expertise needed to properly take various measurements.

The foregoing general description and the following detailed description are exemplary and explanatory only and are not restrictive of the disclosure.

SUMMARY

One method includes: receiving a configurable parametric model of a user-specific eyewear product comprising a frame portion and a lens portion, wherein geometric parameters of the configurable parametric model are based on geometric features of a user's anatomy; receiving media data of a user, the media data including the user's response to visual cues; detecting the position of the user's eyes from the received media data; determining optical information of the user based on the detected position of the user's eyes; and generating an updated configurable parametric model by modifying the received configurable parametric model based on the determined optical information.

In accordance with another embodiment, a system for generating a parametric model of a user-specific eyewear product: a data storage device storing instructions for generating a parametric model of a user-specific eyewear product; and a processor configured for: receiving a configurable parametric model of a user-specific eyewear product comprising a frame portion and a lens portion, wherein geometric parameters of the configurable parametric model are based geometric features of a user's anatomy; receiving media data of a user, the media data including the user's response to visual cues; detecting the position of the user's eyes from the received media data; determining optical information of the user based on the detected position of the user's eyes; and generating an updated configurable parametric model by modifying the received configurable parametric model based on the determined optical information.

In accordance with another embodiment, a non-transitory computer readable medium for use on a computer system containing computer-executable programming instructions for performing a method for generating a parametric model of a user-specific eyewear product, the method comprising: receiving a configurable parametric model of a user-specific eyewear product comprising a frame portion and a lens portion, wherein geometric parameters of the configurable parametric model are based geometric features of a user's anatomy; receiving media data of a user, the media data including the user's response to visual cues; detecting the position of the user's eyes from the received media data; determining optical information of the user based on the detected position of the user's eyes; and generating an updated configurable parametric model by modifying the received configurable parametric model based on the determined optical information.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

FIG. 1 is a block diagram of an exemplary system and network for generating an eyewear frame and lens geometry that is customized to a user's anatomy and optimized for optical performance, according to an exemplary embodiment of the present disclosure.

FIG. 3 depicts an exemplary fitting and/or preview of an eyewear frame to a multifocal lens, according to an embodiment of the present disclosure.

DESCRIPTION OF THE EMBODIMENTS

Figure 2A:
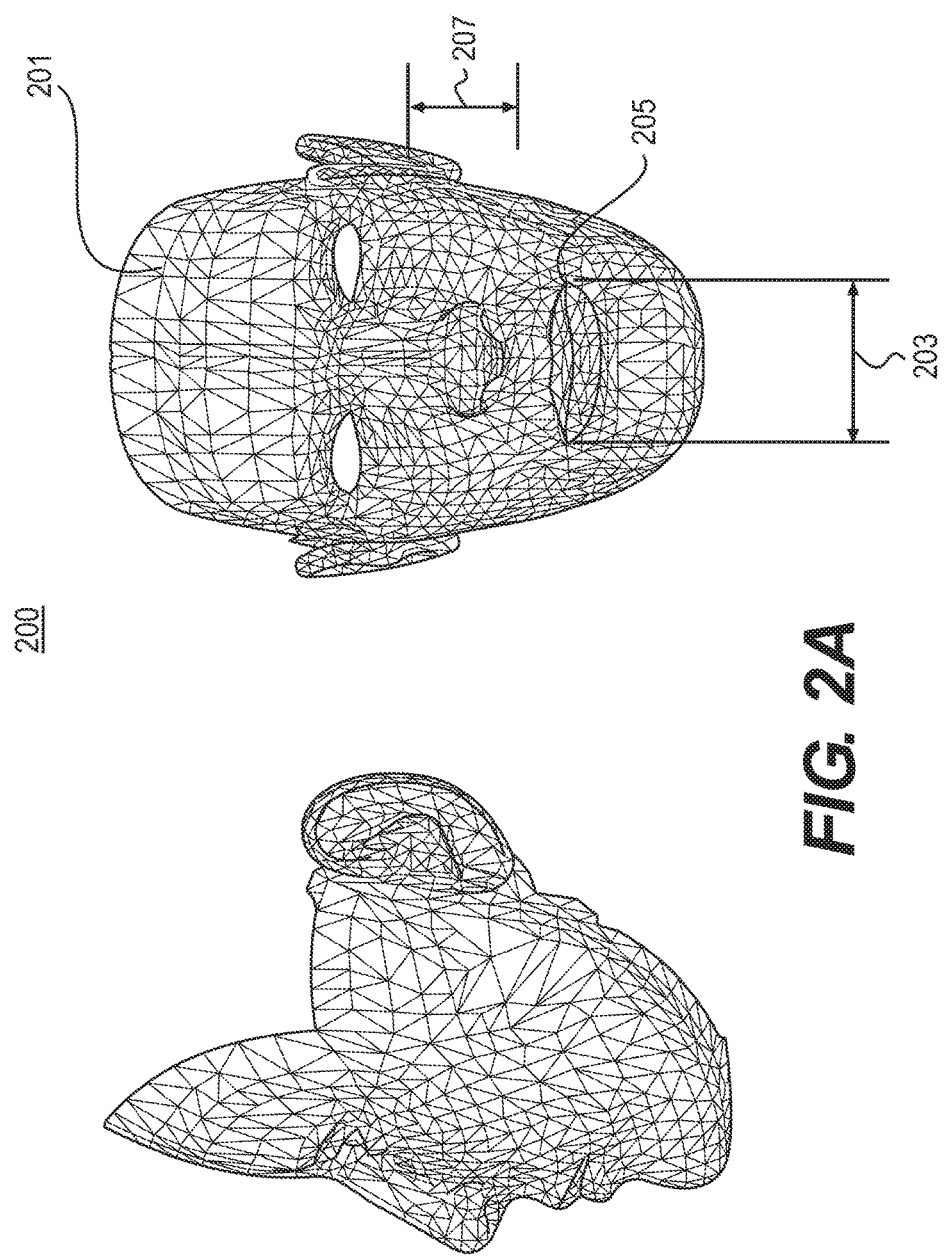
FIG. 2A depicts an exemplary anatomic model, according to an embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Embodiments of the present disclosure relate to systems and methods for creating, manufacturing, and delivering products customized to the needs and preferences of an individual user by building the product from a specification that is generated from automatic and/or user-guided, user-specific anatomic and preference profiles. Particular embodiments of the present disclosure relate to systems and methods for generating an eyewear frame and lens geometry that is customized to a user's anatomy and optimized for optical performance.

In one embodiment, the present disclosure may include systems and methods for generating eyewear for a specific individual. For example, the present disclosure may include systems and methods for producing customized eyewear by constructing a user's multi-focal or progressive lenses and frames in accordance with the user's anatomy and optimized for optical performance. For example, the frames may be shaped to align with, or mold or contour relative to a user's facial anatomy. In one scenario, the present disclosure may include generating or receiving a model of the user's anatomy (e.g., facial anatomy), and building a configurable parametric model of eyewear frames that form to geometric features of the model of the user's anatomy. In another example, the lenses of the eyewear may be shaped based on a user's optical information. Optical information may include information that contributes to producing or procuring the user's ideal optical lens, e.g., prescription information (power, sphere, axis, centration, add power, positioning, etc), lens type, lens material, lens tint, lens thickness, lens curvature, base curvature, lens size, optical design parameters (e.g., interpupillary distance for distance viewing, interpupillary distance for near vision, vertex distance, face wrap, eyewear and frame outline, segment height, optical height, etc.), corrective needs of the user (e.g., correction for astigmatism or presbyopia), the user's viewing habits, etc. In one embodiment, optical information may include information organized into multiple categories: information regarding how the lens fits in the frame (e.g., a change to the parametric frame may correspondingly adjust the parametric lens, information regarding the optical parameters of the lens (independent of the shape of the frame), information on the lens (independent of the frame), digital progressive lens design parameters or principles, "position of wear" variables (e.g., variables that are a result of how a frame fits on the anatomic features of a user), etc.

Information regarding how the lens fits in the frame may include one or more of the following: A size (width), B size (height), lens circumference, distance between innermost point of the edged/cut profile of the left lens shape to the innermost point on the profile of the edged/cut right lens shape (DBL), frame wrap/base curve, traced outline (e.g., an actual 2D or 3D shape of the edged/cut contours of the lens that may match corresponding lens holes in the frame, lens bevel or groove type (and dimensions), lens bevel or groove positioning within the edged thickness (side) of the lens (e.g., distance or percentage from front surface of lens, base curve of bevel (e.g., follow lens or deviations to ideal curve), etc.

Information regarding the optical parameters of the lens (independent of the shape of the frame) may include one or more of the following: prescription (e.g., power, sphere, axis, add power, etc.), lens type (e.g., single vision, bi-focal, tri-focal, progressive, etc.), centration (e.g., monocular interpupillary distance for distance viewing, monocular interpupillary distance for near viewing (e.g., reading), binocular interpupillary distance, etc.). Monocular interpupillary distance may include the distance from each eye to the center plane of the nose. Monocular near pupillary distance (as opposed to binocular interpupillary distance) may yield information as to how a user biases their preferred reading position, e.g., with respect to the right and left eye. Some users may be more right-eye dominant, and actually prefer to read an object to the right of center. Monocular $P_d$ may capture this user bias if it is measured while a user is reading an object located at their ideal reading location, for instance.

Information on the lens (independent of the frame) may include one or more of the following: base curve, lens material (e.g., CR-39, polycarbonate, 1.60, Trivex, etc.), lens material index (e.g., 1.49, 1.56, 1.60, etc.), center thickness, lens coatings (e.g., anti-reflection, superhydroscopic, anti-scratch, anti-static, etc.), lens tinting, and/or other lens attributes (e.g., polarizing, photochromatic, blue light blocking, etc.).

Digital progressive lens design parameters or principles may include one or more of the following: progressive lenses may be expected to introduce unwanted peripheral distortion, certain lens designs may be optimized for various use cases in order to optimize the optical design for that use case at the expense of distortion in areas of the lens not used for that use case (e.g., a progressive lens for all-around use may balance the design for both distance and reading, and a progressive lens for mainly reading use may optimize the reading area at the expense of distance viewing, corridor length (e.g., length of the transition from distance to reading, where designs may be optimized to yield a lens when a long corridor is not possible (e.g., if the intended frame is not very tall)), etc.

"Position of Wear" variables may include one or more of the following: vertex distance (e.g., distance from back of the lens to the pupil as the lens is positioned in the frame and the frame on the face of the user), pantoscopic tilt (e.g., the downward tilt of the lens as it is positioned in the frame and sitting on the face with respect to the pupil), frame wrap (e.g., the inward tilt of the lens as the lens is positioned in the frame and as the frame is positioned on the face), optical height (e.g., vertical distance from bottom of the lens to the user's pupil or iris), segment height (e.g., for a bifocal or trifocal lens, the segment height may include the vertical distance from bottom of lens to top of the bifocal (or tri-focal) reading region. For a progressive lens, the segment height may include the vertical distance from the bottom of the lens to the starting point of the transition from distance to reading. This height may be adjusted based on the desired reading position of a user), monocular distance (e.g., since left and right lenses may differ based on where a user's pupils and/or irises are with response to the center of the user's nose), etc.

Advanced "digitally-compensated" progressive lens designs can adjust the front and/or back surfaces of the lens in response to the "Position of Wear" variables, for instance, in order to optimize the optical performance of a lens (and reduce unwanted optical distortion) for a given frame and user. But the compensation may be increased if the frame is adjusted to hold the lens in a non-optically-ideal position. There may be a limit to the amount of digital compensation that can be achieved. Certain frame shapes may restrict how well a resultant lens can optically perform. For example, too small of a B-size (e.g., a narrow height of a lens) may often does not allow for a large enough reading section for a bi-focal or progressive lens, or such a B-size may entail a very short progressive corridor length. Likewise, the more the frame wrap, the more distortion may be introduced (or the more digital compensation may be desired in order to reduce said distortion).

By allowing the parametric adjustment of a frame in response to a lens, the disclosed systems and methods may adjust the frame to position the lens on the users face with the best optical performance. For example, the wrap and curve of a frame can be adjusted to correspond to the best optical design for a user. In one exemplary case, the pantoscopic tilt of the frame can be adjusted to position the angle of the lens ideally, given how the frame may sit on the face and given the user's preferred reading location. Alternately or in addition, the temple angles of the frame can be adjusted based on the base curve of the lens so the temples may be correctly positioned with respect to the user's ears. If a user prefers to use a stock lens (e.g., to reduce cost), the disclosed systems and methods may parametrically adjust a frame in order to position the stock lens to achieve the best optical performance.

A user's viewing habits may include a facial location at which the user prefers to wear his or her glasses (e.g., whether a user prefers to wear glasses low on the bridge of their nose or high on the bridge of their nose), the tilt through which a user looks at objects through the lenses, whether the user uses the glasses for focusing on close objects (e.g., during reading), distant objects (e.g., during sports), or varying ranges (e.g., looking at dashboard signals and road signs while driving), etc. For instance, if a user regularly reads while looking down at an extreme angle, he or she may benefit from having a higher pantoscopic tilt, and/or a reading region that is positioned lower on the lens, and/or lenses that are taller, and/or lenses positioned lower on the face. In the present disclosure, a frame may be customized to accommodate taller lenses, and/or a frame geometry constructed to position the lenses lower on the user's face, and/or a reading region of the lenses that is positioned low on the lenses. In another instance, if a user's nose bridge is very low, he or she may have trouble seeing through the lenses at her desired reading position and distance because normal frames may position the optics too close to her face. In the present disclosure, the vertex distance of the customized product could be optimized to place the lenses at an ideal distance from the user's eyes.

In addition to describing exemplary systems and methods for generating the customized eyewear or generating models of the customized eyewear, the present disclosure also includes exemplary systems and methods for presenting users with a preview of their customized eyewear. Such previews may include displays of how the user may look while wearing the eyewear and/or displays of how the user may view objects while looking through the lenses of the eyewear. In one embodiment, the displays may include interactive displays, where the user may further modify geometric, aesthetic, and/or optical aspects of the modeled and displayed eyewear.

The present disclosure also includes exemplary systems and methods for assessing a user's optical information and creating customized eyewear for the user based on the determined optical information. For example, the present disclosure includes exemplary systems and methods for evaluating a user's viewing habits. In one embodiment, an assessment may include providing a set of visual displays and analyzing the user's response. In evaluating the user's response to various visual cues, the assessment may infer viewing habits and/or optical characteristics (e.g., line of sight distance, etc.) of the user. The present disclosure further includes systems and methods for determining parameters for customizing an eyewear product to suit the user's anatomic and optical comfort, based on the determined viewing habits and/or optical characteristics. The present disclosure further includes systems and methods for manufacturing the customized lenses and frames.

While the embodiments of the present disclosure will be described in connection with creating, producing, and delivering custom eyewear, it will be appreciated that the present disclosure involves the creation, production, and delivery of a wide variety of products that may relate to the anatomical or physical characteristics of the user as well as the user's preferences for a particular product. It will be appreciated that describing the disclosed embodiments in terms of the creation, production, and delivery of eyewear carries a large number of similarities to the creation, production, and delivery of a wide variety of products customized to the features and desires of the user. What follows therefore describes the disclosed embodiments in terms of eyewear, it being understood that the disclosure is not so limited.

The following descriptions are for explanatory purposes to help define the breadth of words used herein. These definitions do not limit the scope of the disclosure, and those skilled in the art will recognize that additional definitions may be applied to each category. By way of definition as used herein, image data may include two-dimensional (2D) image(s), digital images, video, series of images, stereoscopic images, three-dimensional (3D) images, images acquired with standard light-sensitive cameras, images acquired by cameras that may have multiple lenses, images acquired by multiple independent cameras, images acquired with depth cameras, images acquired with laser, infrared, or other sensor modalities. Alternately or in addition, depth information may be received or derived from depth sensor(s) independent of image capture (e.g., depth data from a 3D point cloud with no image(s) associated).

In one embodiment, a depth sensor may include a sensor that captures 3D point cloud data and may also create a mesh from said point clouds (absent image capture). In some instances, using depth sensor data alone (e.g., without image capture) may have various limitations. For example, depth data from a depth sensor, alone, may be unable to detect or provide information on the center of a user's pupil. The depth sensor may provide a 3D point cloud data (or a mesh)

that corresponds the smooth curvature of the user's eyeball, but since the pupil has no discernible 3D features, depth information alone may fail to provide the location of the user's pupil. Meanwhile, image data (e.g., from an image capture device) may provide a position/location of a user's pupil, e.g., by detecting the contrast difference between the white portion of the user's eyeball and the dark pupil (or iris).

Some described exemplary systems and methods may include depth cameras, for instance, cameras that may operate combined depth sensors in conjunction with image sensors to capture a 3D point cloud, form a mesh, and/or apply a texture from the image data (e.g., to correctly paint a physical final eyewear model). Alternately or in addition, the described exemplary systems and methods may include depth cameras that may be combined with depth sensors and image sensors, which may output 2D images. In such images, each pixel may be associated with a depth value (e.g., a distance value from the camera). Outputs from either or both of these exemplary scenarios may be used in the described embodiments.

Various mobile devices (e.g., mobile phones) have (or may have) one or more depth sensors and one or more image sensors, e.g., as independent sensors. In one embodiment, the disclosed systems and methods may detect inputs from each of the two types of sensors (e.g., depth sensors and image sensors) and process the sensor data into data that may be generated by a single integrated "depth camera."

Computer systems may include tablets, phones, desktops, laptops, kiosks, servers, wearable computers, network computers, distributed or parallel computers, or virtual computers. Imaging devices may include single lens cameras, multiple lens cameras, depth cameras, depth sensors, laser cameras, infrared cameras, or digital cameras. Input devices include touchscreens, gesture sensors, keyboards, mice, depth cameras, audio speech recognition, and wearable devices. Displays may include panels, LCDs, projectors, 3D displays, 2D displays, heads-up displays, flexible displays, television, holographic displays, wearable displays, or other display technologies. Previewed images in the form of images, video, or interactive renderings may include images of the user superimposed with product model images, images of the user superimposed with rendering of product model, images of the anatomic and product models of the user, etc. Anatomic models, details, and dimensions may include length of features (e.g., length of nose), distance between features (e.g., distance between ears), angles, surface area of features, volume of features, 2D contours of features (e.g., outline of wrist), 3D models of features (e.g., surface of nose or ear), 3D coordinates, 3D mesh or surface representations, shape estimates or models, curvature measurements, or estimates of skin or hair color definition, and/or estimates of environmental factors (e.g., lighting and surroundings). For example, disclosed embodiments may include analyzing a scene (e.g., of image data), computing lighting of the scene, and rendering customized glasses lenses with the same lighting. In such a display, the glasses and lenses may be previewed in a display realistically mimicking the image data. For example, a user may capture image data of himself or herself, and then preview a scene of himself or herself wearing customized glasses, as if looking in a mirror or watching footage of himself or herself, at the same scene as in the captured image data. In one scenario, the embodiments may further include capturing the surroundings (e.g., simultaneously, using the same image capture) OR simultaneously capturing images from the REAR camera at the same time that a front camera captures image data of the user. In the latter instance, images from the rear camera may provide realistic reflections rendered on the lens that correspond to the environment in which the capture was conducted. For example, if a user captures a video at the beach, a preview may include a rendering of the beach not only behind the user (captured as part of the images used to build the user 3D model and then superimposed back on those images), but the preview may also include the beach reflected in the lenses.

A model or 3D model may include a point-cloud, parametric model, a texture-mapped model, surface or volume mesh, or other collection of points, lines, and geometric elements representing an object. Manufacturing instructions may include step-by-step manufacturing instructions, assembly instructions, ordering specifications, CAM files, g-code, automated software instructions, co-ordinates for controlling machinery, templates, images, drawings, material specifications, inspection dimensions or requirements, etc. A manufacturing system may include a computer system configured to deliver manufacturing instructions to users and/or machines, a networked computer system that includes machines configured to follow manufacturing instructions, a series of computer systems and machines that instructions are sequentially passed through, etc. Eyewear may include eyeglass frames, sunglass frames, frames alone, lenses alone, frames and lenses together, prescription eyewear (frames and/or lenses), non-prescription (piano) eyewear (frames and/or lenses), sports eyewear (frames and/or lenses), or electronic or wearable technology eyewear (frames and/or lenses).

A computer system may obtain an anatomic model of a user's anatomy. The anatomic model may include but is not limited to a parametric or shape model, a 3D mesh or point cloud, or a set of points or measurements.

Referring now to the figures, FIG. 1 is a block diagram 100 of an exemplary system and network for generating an eyewear frame and lens geometry that is customized to a user's anatomy and optimized for optical performance, according to an exemplary embodiment of the present disclosure. Specifically, FIG. 1 depicts an exemplary computer system 101, in communication with an image capture device 103, a display 105, and a manufacturing system 107. In one exemplary embodiment, computer system 101 may include but not be limited to a tablet, phone, desktop, laptop, kiosk, or wearable computer. The computer system 101 may further comprise server systems that may include storage devices for storing received images and data and/or processing devices for processing received image and data. In one embodiment, computer system 101 may be in communication with an image capture device 103. Image capture device 103 may include but not be limited to a single-lens camera, video camera, multi-lens camera, a multi-camera, IR camera, laser scanner, interferometer, etc. The image capture device is henceforth referred to as "camera".

In one embodiment, computer system 101 may also be in communication with a display 105. The display 105 may include but is not be limited to LCD screens, flexible screens, projections, holographic displays, 2D displays, 3D displays, heads-up displays, or other display technologies. The computer system 101 may include an input device for controlling the computer system 101, including but not limited to a touchscreen, keyboard, mouse, track pad, or gesture sensor. The input device may be part of the display 105 and/or communicate with the display 105. The computer system 101 may be further configured to provide an interface for a user (e.g., a customer, a user similar or related to the customer, an eyewear professional, etc.) to view, customize, browse, and/or order custom products. This interface may be rendered by display 105, which may be either part of, or remote, from the computer system 101, in various embodiments.

In one embodiment, computer system 101, image capture device 103, and/or display 105 may communicate to collect user information (e.g., user anatomy and optical information provided via image data), analyze the collected user information, and generate models of customized eyewear based on the collected user information. For example, optical information may be received via a direct transfer of the user's prescription data, received via word recognition of an image/photograph of the user's prescription, and/or derived from other imaging of the user's anatomy. The computer system 101 may be configured to connect to a network 109 or other systems for communicating and transferring data. In one embodiment, network 109 may provide communication between one or more image capture devices, displays, and/or input devices, and the computer system 101. For example, network 109 may be a bus and/or other hardware connecting one or more of components and modules of one or more image capture devices, displays, and/or input devices, and the computer system 101. Alternately or in addition, the computer system 101 may be configured to include the image capture device 103, one or more other image capture devices, the display 105, one or more other displays, input devices, and/or a combination thereof. The computer system 101 may include or be in communication with any combination of image capture devices, displays, input devices, or other computer system(s). In some embodiments, a user or an eyewear professional may be in communication with or inputting data into computer system 101. Such data may include user anatomy and/or viewing habits.

The computer system 101 may be configured to connect (e.g., via network 109) to other computer system(s), including but not limited to servers, remote computers, etc. The other computer system(s) may be connected to or in control of the manufacturing system 107. In one embodiment, manufacturing system 107 may receive manufacturing instructions (e.g., from computer system 101). For example, models of customized eyewear determined by computer system 101 may be converted into manufacturing specifications (e.g., either by the computer system 101, manufacturing system 107, or a combination thereof). The manufacturing system 107 may then produce a physical version of the customized eyewear based on the modeled customized eyewear and/or prompt the delivery of the customized product to the user. For example, manufacturing system 107 may produce and/or deliver customized products using any of the methods and systems described in detail in U.S. patent application Ser. No. 14/466,619, filed Aug. 22, 2014, which is incorporated herein by reference in its entirety.

FIG. 2A depicts an exemplary anatomic model 200, according to an embodiment of the present disclosure. In one embodiment, a computer system may receive an anatomic model of a user, who may upload, input, and/or transfer his or her anatomic data to the computer system. For example, a user may transfer a photograph or video of his/her facial features to the computer system, e.g., from another computer system or an image capture device. In some scenarios, the computer system may receive measurements input by a user, e.g., the computer system may provide a display including one or more prompts or instructions, guiding a user to submit various forms of anatomic data. In an exemplary embodiment, the computer system may generate an anatomic model of the user based on image data and/or measurement data of the user's anatomy. For example, the computer system may receive image data, detect and quantify geometric measurements of one or more facial features from the received image data, and reconstruct an anatomic model of the face based on methods described in U.S. patent application Ser. No. 14/466,619, filed Aug. 22, 2014, which is incorporated herein by reference in its entirety.

For example, anatomic model 200 may be comprised of a mesh 201. The resolution of the mesh 201 may be altered based on curvature, location, and/or features on the user's face, etc. For example, mesh 201 around the eyes and nose may be higher resolution than mesh 201 at the top of the head. In an exemplary embodiment, the anatomic model 200 may include the front and side face area, though in other embodiments, the anatomic model 200 may model the entire head, while including more detail at the modeled eyes and nose. Alternative representations may include point clouds, distance maps, image volumes, or vectors.

In an exemplary embodiment, a generalized quantitative anatomic model may be distorted to fit the user's face, e.g., based on anatomic data input by the user. The model 200 may be parameterized and represented as a mesh, with various mesh points affected by adjusting parameters. For example, mesh 201 may include various mesh elements, such that one parameter may constrain or influence another parameter. For example, a parameter (e.g., user expression) may influence the length 203 of mouth feature 205, the height of cheek feature 207, and by extension, the portion of lenses that a user may be looking through. In this example, if the parameter influencing length 203 were adjusted, then the appropriate elements of the mouth 205 and cheek feature 207 (and lens portion) would adjust coordinates in order to match the parameter specified. Other models, e.g., a shape model, may have generalized parameters like principal components that do not correspond to particular features but allow the generalized anatomic model to be adapted to a plurality of different face sizes and shapes.

In one embodiment, a computer system (e.g., computer system 101) may analyze received image data to iteratively perform a sequence of feature detection, pose estimation, alignment, and model parameter adjustment. A face detection and pose estimation algorithm may be used to determine a general position and direction the face is pointing toward, which may aid in model position and alignment. Machine learning methods may be used to train a classifier for detecting a face as well as determining the pose of the head in an image that is post-processed to define various features, including but not limited to Haar-Like or Local Binary. Training datasets may include of images of faces in various poses that are annotated with the location of the face and direction of pose, and also include specific facial features. The output may include a location of the face in an image and a vector of the direction of head orientation, or pose.

The computer system may further receive or detect the 3D position and 3D angle and/or 3D orientation (e.g., rotation, tilt, roll, yaw, pitch, etc.) of an imaging device relative to the user, while capturing the received image data. In one embodiment, the position and/or orientation of the imaging device may be transmitted to the computer system, e.g., as part of the image data. In another embodiment, the position and/or orientation of the imaging device may be detected from the image data.

In one embodiment, the computer system may iteratively define more detailed facial features relevant to eyewear placement and general face geometry, e.g., eye location, pupil and/or iris location, nose location and shape, ear location, top of ear location, mouth corner location, chin location, face edges, etc. Machine learning may be used to analyze the image to detect facial features and edges. In one embodiment, the generalized quantitative anatomic model parameters may be aligned and adjusted to the detected/located facial features, minimizing the error between the detected feature location and the mesh. Additional optimization of the generalized quantitative anatomic model may be performed to enhance the local refinement of the model using the texture information in the image.

In an exemplary embodiment, the generalized quantitative anatomic model may include parameters that influence features including but not limited to eye location, eye size, face width, cheekbone structure, ear location, ear size, brow size, brow position, nose location, nose width and length and curvature, feminine/masculine shapes, age, etc. An estimation of the error between the detected features and model may be used to quantify convergence of the optimization. Small changes between adjacent images in a dataset (e.g., from video image data) may be used to refine pose estimation and alignment of the model with the image data. The process may iterate to subsequent image frames.

Those skilled in the art will recognize there are many ways to construct and represent quantitative information from a set of image data. In another embodiment, a user quantitative anatomic model may be generated without a generalized anatomic model. For example, the computer system may use structure from motion (SFM) photogrammetry to directly build a quantitative anatomic model. The features detected in multiple images, and the relative distances between the features from image-to-image may be used to construct a 3D representation. A method that combines a generalized shape model with subsequent local SFM refinement may be utilized to enhance local detail of features, e.g., a user's nose shape.

In another embodiment, user quantitative anatomic model may include a point cloud of key features that are detected. For example, the computer system may detect and track facial landmarks/features through one or more images. Exemplary facial landmarks/features may include the center of the eyes, corners of the eyes, tip of the nose, top of the ears, etc. These simple points, oriented in space in a dataset, may provide quantitative information for subsequent analyses. The point cloud quantitative information may be obtained using the methods previously mentioned, or with other methods, e.g., active appearance models or active shape models.

Technologies including depth cameras or laser sensors may be used to acquire the image data, and directly produce 3D models (e.g., a 3D scanner), by their ability to detect distance. Additionally, the use of out of focus areas or the parallax between adjacent images may be used to estimate depth. Additionally, data acquired via a depth sensor may be combined with images/image data captured from an image sensor, and the two datasets may be combined via the methods described herein in order to refine and achieve a higher-accuracy face mesh and/or camera positions/orientations.

Alternatively, the user quantitative anatomic model and dimensions may be derived from a pre-existing model of the user's face. Models may be acquired from 3D scanning systems or imaging devices. The computer system may receive user anatomic models via digital transfer from the user, e.g., by non-transitory computer readable media, a network connection, or other means.

Figure 2B:
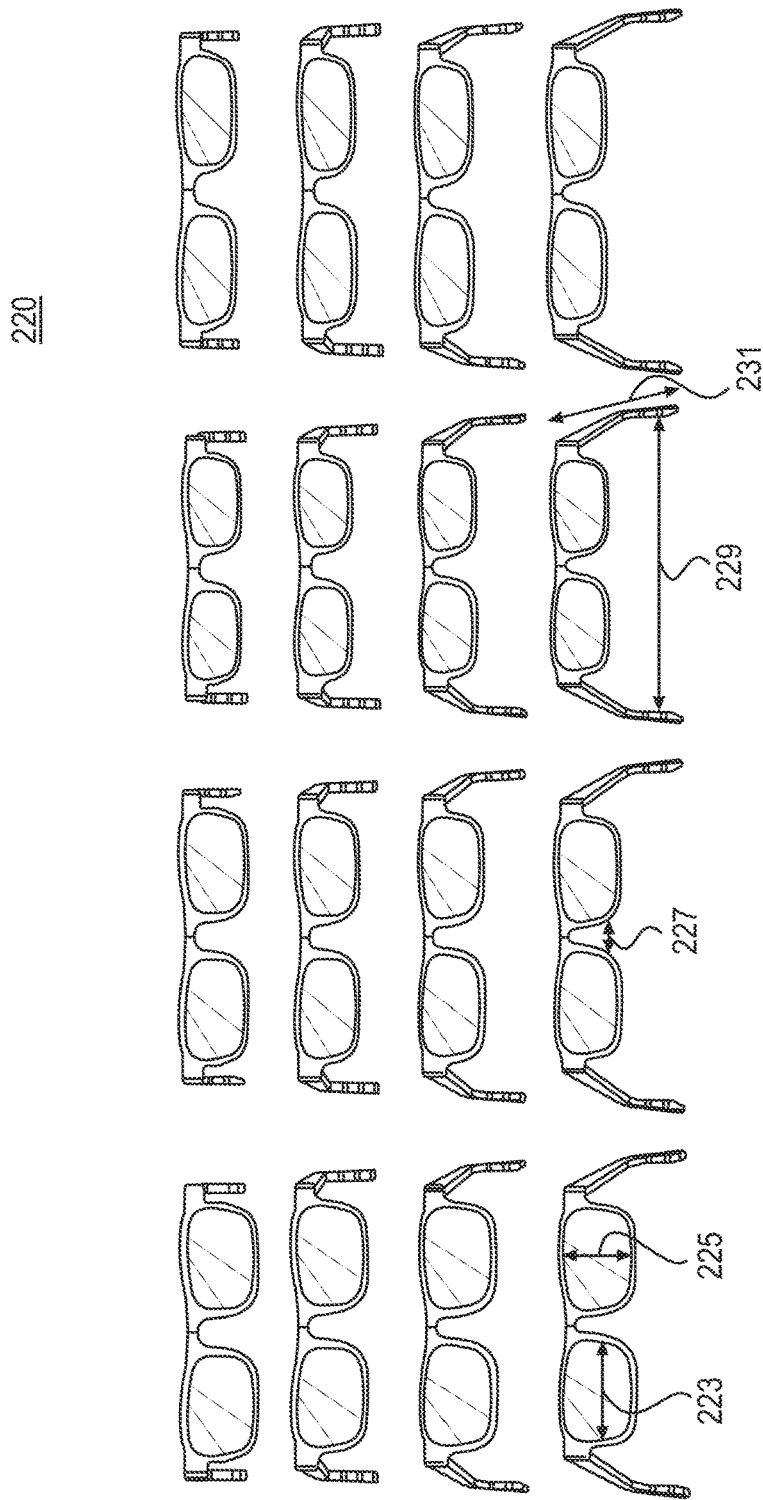
FIG. 2B depicts an exemplary parametric model of a user-specific eyewear product, according to an embodiment of the present disclosure.

FIG. 2B depicts an exemplary parametric model 220 of a user-specific eyewear product, according to an embodiment of the present disclosure. The computer system may obtain or generate at least one parametric model of a user-specific eyewear product including a frame portion and a lens portion. FIG. 2B includes various examples of configurations and shapes that may be achieved by changing one or more of parameters of the parametric model 220. The parametric model 220 may include a representation of the eyewear product that may be modified to alter properties, including shape, size, color, finish, etc. The parametric model 220 may be adapted to a variety of shapes, sizes, and configurations to fit a diversity of face shapes and sizes. For example, nose pads of an initial parametric model of the eyewear product may not match the contour of the user's nose (e.g., from a user anatomic model). The initial parametric model may instead intersect with the surface of the nose if the initial parametric model is aligned with or overlaid over the user anatomic model. The present computer system may configure or modify the initial parametric model such that the nose pads match the contour and angle of the user's nose from the user anatomic model, e.g., the nose pads are modified to sit flush against the surface of the modeled user's nose. In some embodiments, parametric model 220 may be generated directly from user anatomic data, without obtaining an initial (e.g., generic) parametric model and modifying the initial model based on the user anatomic data. For example, parametric model 220 may be generated with a provided 3D model of the user's face/anatomic measurements of the user's face, with a 3D mesh or point cloud (e.g., from a depth sensor), and/or another method where a parametric model may be generated without modifying a pre-existing one.

In some embodiments, the parametric model 220 may enable adjustment of at least one parameter, while allowing constraints to be enforced on other parameters so the model may be locally adapted, for example, by adjusting the width and angle of the nose pads on the customized eyewear product without changing anything else about the eyewear product. FIG. 2B shows exemplary parametric model 220 configured to 16 variations. The exemplary configurations depict variations of eyewear lens width 223, lens height 225, nose bridge width 227, the distance 229 between the temples where the earpieces of the frame may contact a user's ears, the distance 231 from the front of the frame to the user's ears, and other minor dimensions. In the illustrated embodiment, the material thickness and hinge size and location may remain unchanged. The parametric configuration may enable the eyewear design to be highly configurable while remaining manufacturable. For example, a manufacturer may use one hinge design and a single selected material thickness for all these designs and more, yet still allow massive customization of the underlying shape and size.

The parametric model 220 may include constraints that prevent certain parts/regions from being altered into a design that is no longer optimal to manufacture. For example, the minimum thickness of parts may be limited to ensure structural strength, and the minimum thickness around the lenses may be limited to ensure the lenses can be assembled into the eyewear without the eyewear breaking or the lenses not being secure within the frame. Furthermore, the hinge locations and optical surface of the lenses may be constrained to ensure that the modeled eyewear would fit and sit at a proper angle for a user. Additionally, certain features may be related due to symmetry or cascading effects; for example, if the computer or user adjusted the width or thickness of one part of the rim, the entire rim on both sides may adjust to ensure a symmetric and attractive appearance. The cascading effects may take into account how symmetry to the frame extends or does not extend to the lenses. For example, two lenses in an eyewear frame may vary based on what each lens corrects. A parametric model 220 may be configured such that the thickness of the frames is adjusted according to the thicker of the two lenses, so that the resulting eyewear remains feeling balanced to the user, even though a frame of a lesser thickness may be sufficient to contain the thinner of the two lenses. Parametric models may be generated and customized using any of the systems and methods described in detail in U.S. patent application Ser. No. 14/466,619, filed Aug. 22, 2014, which is incorporated herein by reference in its entirety.

In addition to geometry, the parametric model 220 may include parameters for the surface finish, color, texture, and other cosmetic properties. Parametric model 220 may include or be rendered with a multitude of materials, paints, colors, and surface finishes. Various rendering techniques known to those skilled in the art, such as ray tracing, may be used to render the eyewear and lenses in a photorealistic manner, showing how the eyewear of the parametric model 220 may appear when manufactured. For example, parametric model 220 may be texture mapped with an image to represent the surface or rendered with texture, lighting, and surface properties, including reflectance, transmission, subsurface scattering, surface, or roughness to represent photorealistic appearance of eyewear. Textures used for reflection may be based on generic environment maps, or they may be generated from data captured by an image capture device. Environmental lighting parameters may be extracted from the data captured by the image capture device and used to render the frame and lenses with the same lighting parameters so that the frames and lenses appear more realistic in rendered previews. The parametric model 220 may further include such lighting and surface properties for lenses of the parametric model 220, based on the lens curvature, thickness, lens material, lens gradation, corrective aspects, etc. Corrective aspects may include whether the lenses are lenses to correct astigmatism, presbyopia, myopia, etc. The lens portion of the parametric model 220 may contain multi-focal lenses, which may include at least two regions of optical correction, e.g., bifocals, trifocals, progressive, or digitally compensated progressives. For instance, the parametric model 220 may further be adapted so that the lens dimensions fit optical corrections and/or preferences of a user. In one scenario, in addition to the lenses of the parametric model 220 modeling bifocal or progressive multifocal lenses, the placement of the various lens powers of the lenses may vary based on the user's preferences and use of the customized eyewear. Like the modifications to the parametric model 220 that account for the user's anatomy, modifications to the parametric model 220 that serve optical purposes may also enable adjustment of at least one parameter, while constraining other parameters. For example, while the positioning of the magnified reading area within the lens shape may be user-specific for the user's preferences and viewing habits, the actual magnification of this lens section and the gradations (if any) between magnified areas may be constrained.

The parametric model 220 may also account for lens characteristics, for example, in a display shown to a user. For example, one embodiment may include displaying the parametric model 220 on a user interface. For instance, a display of the parametric model 220 may include the aesthetic aspects of the eyeglass (frame and lenses), as well as a simulation of the effects of looking through the lenses, e.g., light distortion, or unmagnified distance and magnified reading areas, peripheral distortion (unwanted astigmatism) of a particular progressive lens design and combination of lens/frame parameters, tint (solid, gradient, and photochromatic), edge thickness, the effects of edge lenticularization, etc Another exemplary simulation may also include displaying how a user may look to others, while wearing the eyewear of the parametric model 220. For example, if the lenses may cause a user's eyes to look smaller to a person seeing the user, the simulation may show the distortion to the user's eyes. Other optical interaction effects, e.g., shadows and reflections, can be displayed on the eyewear and on a 3D model of the user's face (e.g., as shown in FIG. 2A). The calculated thickness of the users lens can also be rendered, in order to allow the user to determine if a higher index (and therefore thinner and more aesthetically pleasing) lens would be appropriate. The parametric model 220 may include hinge points at the temples to allow the temples to flex with respect to the frame front and fit to a model of the user's face. In another embodiment, the parametric model 220 may also account for an elastic modulus (stretch) in the bulk material property of the frame and/or lens, and this elastic property can be dependent on the frame material or lens material selected.

FIG. 3 depicts an exemplary fitting and/or preview of an eyewear frame to a multifocal lens, according to an embodiment of the present disclosure. In one embodiment, FIG. 3 includes an exemplary eyewear frame 301 fitted with multi-focal lenses, where a user's eyes 302 may look through the main portion of the lens intended for distance vision 303. One embodiment may include a display of eyewear frame 301 including, or not including a display of at least the user's eyes 302 (e.g., where looking at the display may be analogous to the user looking in a mirror). In one embodiment, this preview display may further include a simulation of the viewer looking at an object using the distance vision 303 portion of the lenses. In exemplary eyewear frame 304 fitted with multi-focal lenses, the user's eyes 305 may look downward through the exemplary reading section 306 of the lenses to focus on a nearby object situated at location 307. One embodiment may include a display of eyewear frame 304 including, or not including a display of the user's eyes 305 (e.g., where looking at the display may be analogous to the user looking in a mirror). In one embodiment, this preview display may further include a simulation of the nearby object situated at location 307.

In one embodiment, the portion of the lens intended for distance vision 303 and the reading section 306 may be arranged or adjusted, e.g., via modifications to sizes, positions, and/or tilt of each of the portion of lenses. These adjustments may be made as the user moves his or her eyes (e.g., while viewing a preview) and/or as various frames or frame geometries are changed. Previews of the optics/views through the various lenses and lens portions may also be generated and updated as changes are made to the lenses, lens portions, and frames.

Figure 4:
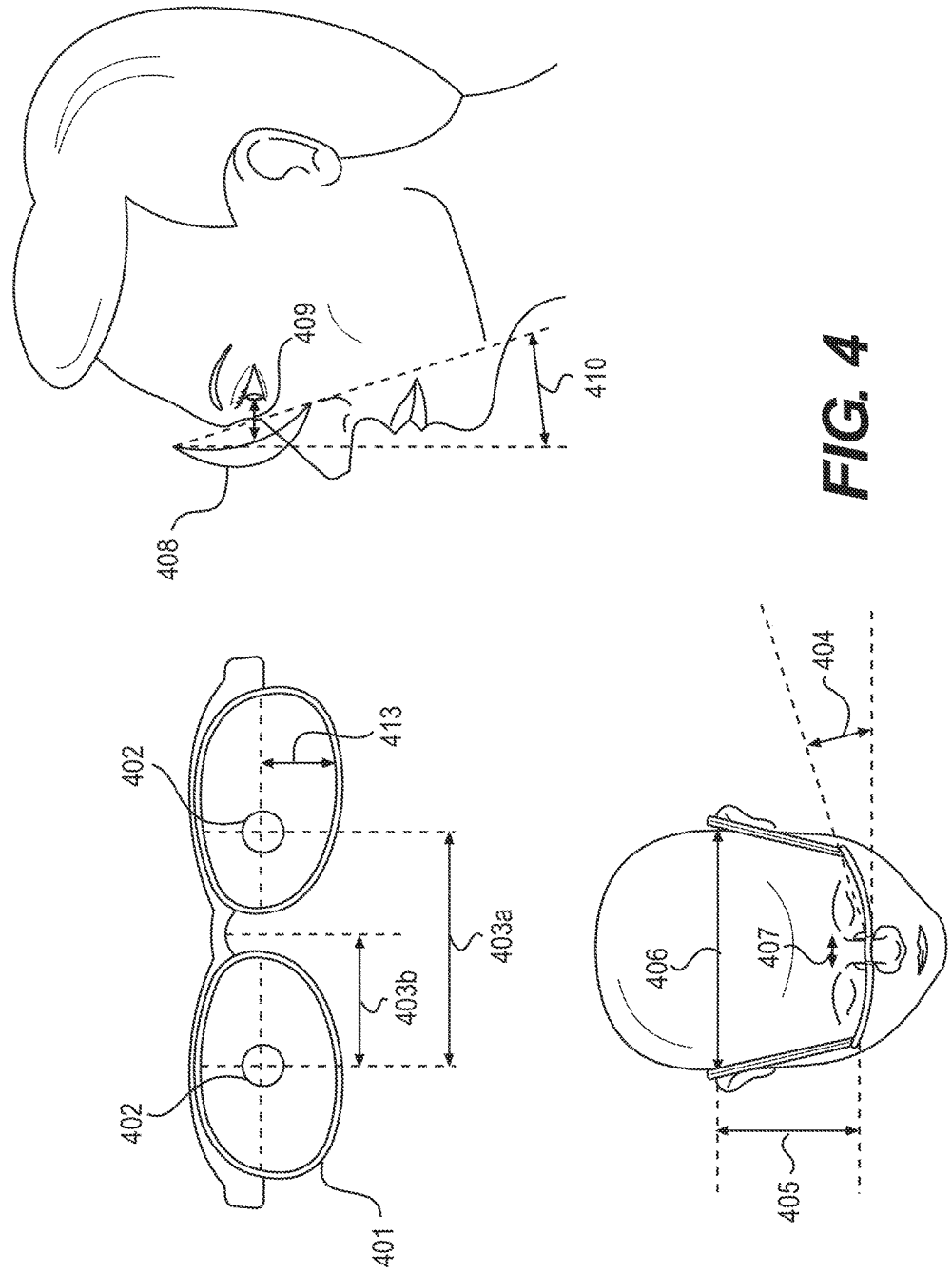
FIG. 4 depicts a detailed exemplary fitting of an eyewear frame to a multifocal lens, according to an embodiment of the present disclosure.

Multifocal optics may involve various inputs to model or optimize, e.g., the positioning of the eyes relative to the frames, the positioning of the eyes relative to different portions of a lens, the positioning of one eye of the user compared to the positioning of another eye of the user relative to the same lens portion, whether a user is looking at a distant object or a nearby object, how each of the user's eyes align with the various lens portions (e.g., based on the height of the user's ears, the positioning of the user's eyes, or the shape of the user's nose, etc.), etc. For example, if the region 306 is too low or too small, then the user may have difficulty looking through it. If the region 306 is not placed in the proper location with respect to the frame 304, then the user may have to rotate, tilt, or position their head in comfortable positions to look through region 306. The lens portion of the model may be a physical representation, e.g., a three-dimensional (3D) model, or it may be a set of numerical parameters for making a lens, e.g., the prescription, base, and other parameters mentioned below. FIG. 4 depicts a detailed exemplary fitting of an eyewear frame to a multifocal lens, according to an embodiment of the present disclosure. The lens portion of the parametric model may also be configurable with parameters including but not limited to: lens base (the curvature of the front of the lens), lens profile 401 (the outer shape of the lens), lens bevel or groove shape, lens prescription, multifocal prescription, add power, coatings, pupillary distance (measured as binocular measurements 403*a* or monocular measurements 403*b* between the center of a user's nose and pupil 402), near pupillary distance (binocular or monocular), size and position of multifocal regions, optical center, segment height (vertical measurement in millimeters from the bottom of the lens to the beginning of the progressive addition on a progressive lens or the top line of a lined bifocal), optical parameters for algorithmic digital "freeform" compensation (e.g., lens configuration 408, vertex distance 409 (distance from the user's eyes/pupils to the back surface of the lens), frame wrap 404, fitting/lens height 413 (vertical location of pupils in the lens), pantoscopic tilt 410 (angle of the lens to the front of the face), etc.), and near pupillary distance ("$P_d$") (the distance between pupils when one focuses on close objects during activities, e.g., reading, or other ranges of focal distance, including intermediate distances in order to read the dashboard when driving).

Digital compensation may also include selecting lens designs based on various use cases. For example, algorithms for estimating lens configurations for a particular user may take into account the eyewear's function to the user or eyewear use cases. For example, eyewear lenses designed for reading glasses will vary from eyewear lenses designed for a user to see distance objects. Exemplary eyewear use cases may also include whether a user is an advanced user or a new user. For example, new users may be better suited for bifocal lenses, and advanced users may be better suited for progressive multifocal lenses. "Digitally compensated" progressive lenses may encompass various lens designs that optimize the optical performance for specific activities (e.g., enhance reading area at the slight expense of reduced distance area, or enhance distance area at the expense of reading, or widen corridor and intermediate area at the expense of full reading area (for the purposes of driving or playing golf)). There are also various designs that may yield short-corridor progressive optics that work with trendy short frame designs, as well as beginner progressives that may reduce the "swim" peripheral effect at the expense of maximizing the distance or reading areas.

Changing any of the previously mentioned parameters may influence the lens design and shape, and may affect the optics of the lens. For example, if the reading distance, near $P_d$, and location of the optics for reading are poorly defined, the user may not be able to comfortably wear their glasses and read. The discomfort may cause the user to move their head and glasses to adjust the position of the optics while trying to focus, or render the optics unusable. Since each user's nose varies in dimensions, there is a great advantage in being able to precisely measure the size and shape of a user's nose, and then custom fit eyewear (lenses and frames) to perfectly fit that anatomy. Optimum comfort of an eyewear's nose pads positioned on a user's nose may be achieved if the two contact surfaces are aligned properly and mate such that there are no high pressure-points and if the eyewear is naturally supported in the proper position by the nose. Each user may have a unique preference as to where on his nose he prefers to wear his eyewear for maximum comfort, aesthetic, or utility. Understanding the quantitative anatomy of the nose may not only allow the frame of a customized piece of eyewear to sit precisely on the nose where desired with maximum comfort, aesthetic, and utility, but also allow a user immediate clarity and comfort in viewing objects for different tasks, according to their habits. For instance, the distance 407 between nosepads of the eyewear may be related to the location of the lenses relative to a user's pupils. The present system may determine the preferred viewing angle at which a user prefers to look at objects through his glasses, given the position of the glasses on his nose. The frame may then be adjusted to position the lenses at the optimum optical angle, and/or the lenses may be shaped in accordance with such habits and preferences of the user (including compensating the optics of a lens for a frame that for aesthetic-reasons may position the lens in a non-optically-optimum location/orientation with respect to the user and/or the user's use case).

FIG. 4 also shows additional measurements of the length of the temples 405 and distance between the temples 406 to achieve a fit with the user's face. Further, the brow, cheekbones, length of nose, and width of the head may provide limitations of where eyewear could fit on a user's face. Other dimensions of the face, including the shape of head, curvatures, the length, shape, and angle of the nose, and more may be used to design a customized frame and lens with optimized comfort and optics for a particular user's use of the eyewear. In other words, generating lenses for a user may take into account user anatomy and user viewing habits to achieve improved or optimum optical performance/clarity for the user.

Figure 5:
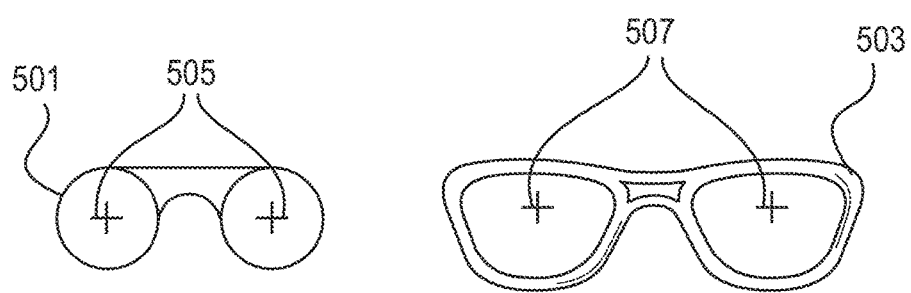
FIG. 5 depicts a detailed exemplary relationship between lenses and frames for optical quality, according to an embodiment of the present disclosure.

FIG. 5 depicts a detailed exemplary relationship between lenses and frames for optimizing optical placement, according to an embodiment of the present disclosure. The locations of the pupils relative to eyewear are important to ensure good optical comfort—an optical goal may be to position the optical center of the lens directly in front of the eye (e.g., pupil and/or iris) when the eye is staring straight-ahead. Incorrect placement can cause unwanted prism effect, which can cause headaches and nausea. In one embodiment, algorithms may aim to optimize lenses, depending on frame shapes. For example, FIG. 5 shows two exemplary eyewear designs: small round frames 501 and large aviator frames 503. The optimal eye locations for frames 501 may be shown as 505, well centered within the eyewear's lens opening—placing the optical center of the lens at this location may result in an evenly thick lens at the edges. The optimal locations for frames 503 may be shown as 507, off-center toward the top of the lens opening. The ideal initial placement of the eyewear may position the user's eyes as close as possible to (e.g. directly behind) these locations, but the resulting lens edge thickness may be non-uniform and for a minus lens to treat myopia, the lens edge may be much thicker the farther the edge is from the optical center of the lens. The thicker the edge of the lens, the less aesthetically desirable is the lens may be. In such a case, switching to a higher-index lens material may reduce the edge thickness, is the higher-index lens material may be more expensive and less optically-clear (e.g., the higher the index, the lower the abbe value, which may translate into a higher chromatic aberration).

In one embodiment, an optimization may be obtained by minimizing the distance between: the center of the eyewear and centerline of the nose; the top of each modeled ear at the location of the intersection of the head and the bottoms of the temples (which sit on the top of the ears); nose pads on the eyewear and surface of the nose; center point of the eyes and the design's optimal eye location; pre-determined offset distance between the brow and/or check bones and the specific eyewear front-frame. As previously discussed, the optimization may also be configured to take into account the function of the eyewear (e.g., eyeglasses for reading versus for seeing distant objects), how thick the eyewear is and how well corresponding frames may hide a thick lens edge, and alternately or in addition, the user's viewing habits when using the eyewear. Frames may also be configured to accommodate, not only the user's anatomy, but the optimized lenses.

Figure 6:
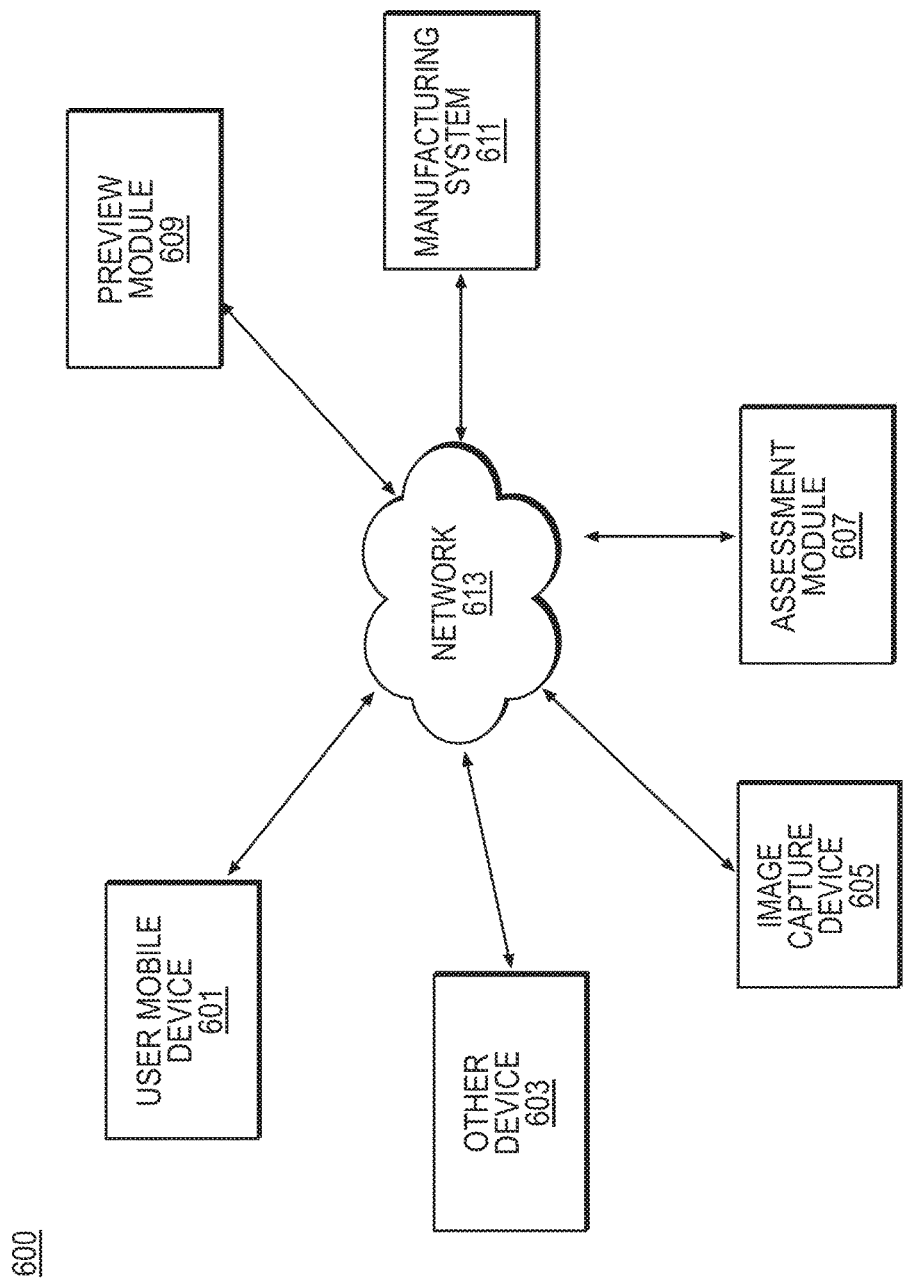
FIG. 6 depicts an exemplary system for assessing a user's viewing habits for optical measurements and generating an eyewear frame and lens geometry customized based on the user's viewing habits, according to an embodiment of the present disclosure.

FIG. 6 depicts a detailed exemplary system 600 for assessing a user's viewing habits for optical measurements, according to an embodiment of the present disclosure. The method and system described to create custom products and eyewear may be useful to an individual user or to a physical location (e.g., a retail store, optometrist office, etc.). The system and method may be controlled, at least in part, by a customer, optician, optometrist, sales-person, or other professional assisting a user with the selection and purchase of the best frame and lenses in an office or retail location or through remote assistance through a computer network. In one embodiment, system 600 may receive data from a user, e.g., via a user mobile device 601. In one embodiment, system 600 may also receive data via one or more other device(s) 603. Such devices may include devices associated with users other than the user, devices associated with professionals, storage devices, etc. Exemplary devices may include physical (e.g., in-store) devices or remote devices (e.g., devices operated by eyewear professionals). In one embodiment, the system 600 may further include one or more image capture device(s) 605. In one exemplary embodiment, the user mobile device 601 and/or the device(s) 603 may be configured to include one or more of the image capture device(s) 605. Image capture device(s) 605 may provide image data for assessing the user's anatomy and/or optical measurements. For example, system 600 may employ a single image capture device 605 or system 600 may employ multiple image capture device(s) 605 (e.g., arranged in a half-circle around the user) to capture the user's anatomy and/or optical measurements from multiple viewpoints and generate one or more anatomic models and/or parametric models of eyewear customized to the user. Exemplary image capture device(s) 605 may include cameras attached to mobile devices, multi-camera systems, depth sensing cameras, depth sensing sensors, etc, or a combination of two or more of the aforementioned devices.

In one embodiment, system 600 may further include an assessment module 607. The assessment module 607 may be configured to assess a user for the optical measurements customized to the user's viewing habits. For example, assessment module 607 may include and/or generate a display including a series of visual assessments and prompts for a user to complete to analyze corrections for the user's vision as well as the user's viewing habits. Assessment module 607 may also capture and/or receive the user's response to the visual assessments and prompts, and analyze the user's response (e.g., correlating/associating the user's response to certain viewing habits). Assessment module 607 may further output optical measurements (e.g., parameters for constructing customized lenses and/or frames for the user, based on the determined user's viewing habits. Further detail on the functions of assessment module 607 is provided in FIGS. 7 and 8.

In one embodiment, assessment module 607 may be installed on user mobile device 601 and/or device(s) 603 (e.g., as an mobile app). In another embodiment, user mobile device 601 and/or device(s) 603 may communicate remotely with assessment module 607. In yet another embodiment, any portion of functions of assessment module 607 may be performed, at least in part, by user mobile device 601 and/or device(s) 603. For example, the assessment module 607 may provide the visual assessments and prompts, which may be displayed to a user by a user mobile device 601. The assessment module 607 may further include directions for the user to capture his or her response to visual assessments and prompts. The assessment module 607 may perform an analysis of the response, and output the analysis for retrieval by the user mobile device 601 and/or other device(s) 603. For example, device(s) 603 may store the information and/or employ machine learning methods to improve knowledge of correlations between viewing habits and optical measurements that improve a user's (or an eyewear product's) optical performance or optical clarity. Any combination or division of operations may be distributed between the user mobile device 601, device(s), image capture device(s) 605, and/or the assessment module 607.

In one embodiment, mobile device 601, device(s) 603, image capture device(s) 605, and/or assessment module 607 may be configured to include and/or work with optometry devices or onboard sensors to measure prescription information (e.g., refraction) and automatically incorporate the measurements into the assessment such that no manual entering of prescription data is needed.

Preview module 609 may include hardware and/or software configured for generating and displaying custom previews, including visualizations of the customized frames or lenses. Exemplary previews may include renderings of the customized eyewear alone, renderings of the user wearing the customized eyewear, and/or previews simulating the user's view though the customized eyewear and/or lenses. The rendering may be overlaid on the user's image data, anatomic model, or as a standalone rendered image of just the frame complete with lenses. In another example, generating a view simulation preview may include rendering a preview of the vision through a custom eyewear model, including the shape, size, and optical properties of a lens. Exemplary previews of this type may include rendering a live or static scene that simulates the user's vision, including but not limited to distortion, area of focus, color, and other optical effects, e.g., how customized lenses may alter a user's vision. In one scenario, such a preview may include providing an augmented-reality preview (over live video or of a stock image) of the customized lenses to demonstrate the customized changes to the lenses and how they will alter a user's vision (by distorting the live video or stock image as if the user were looking through the lenses). This can serve to not only highlight the benefits of customization, but also to guide a user towards the best symbiotic relationship between frame parameters and lens parameters to achieve a combined system that maximizes the user's style, comfort, and optical/visual acuity. This preview can also highlight the differences between subtle optical changes to lens designs (e.g., differences between progressive lens designs for different activities, lengthening the corridor, adjusting the reading area, etc). Capturing data for generating user-specific models (e.g., anatomic and parametric models) and generating previews of customized eyewear is described in detail in U.S. patent application Ser. No. 14/466,619, filed Aug. 22, 2014, which is incorporated herein by reference in its entirety.

Manufacturing system 611 may receive a customized eyewear model (e.g., including parameters for ordering customized eyewear (frames and/or lenses) and user information e.g., via a network 613 or other form of electronic communication such that the manufacturer or manufacturing system 611 may produce the custom eyewear product. In one embodiment, manufacturing system 611 may receive manufacturing instructions (e.g., from system 600) and/or translate data received from system 600 into manufacturing instructions. The manufacturing system 611 may then produce a physical customized eyewear product based on the modeled customized eyewear and/or prompt the delivery of the customized product to the user. Manufacturing customized eyewear is described in detail in U.S. patent application Ser. No. 14/466,619, filed Aug. 22, 2014, which is incorporated herein by reference in its entirety.

The user mobile device 601, device(s), image capture device(s) 605, the assessment module 607, preview device 609, and/or the manufacturing system 611 may communicate via network 613. In one embodiment, network 613 may include the Internet, providing communication through one or more computers, servers, and/or handheld mobile devices, including the various components of system 600. For example, network 613 may provide a data transfer connection between the various components, permitting transfer of data including, e.g., the user's information, optical measurement information, anatomic information, customized parametric model, aesthetic preferences for eyewear, prescription, etc. Alternatively or in addition, network 613 may be a bus and/or other hardware connecting one or more of components and modules of mobile device 601, device(s), image capture device(s) 605, the assessment module 607, preview device 609, and/or the manufacturing system 611.

Figure 7:
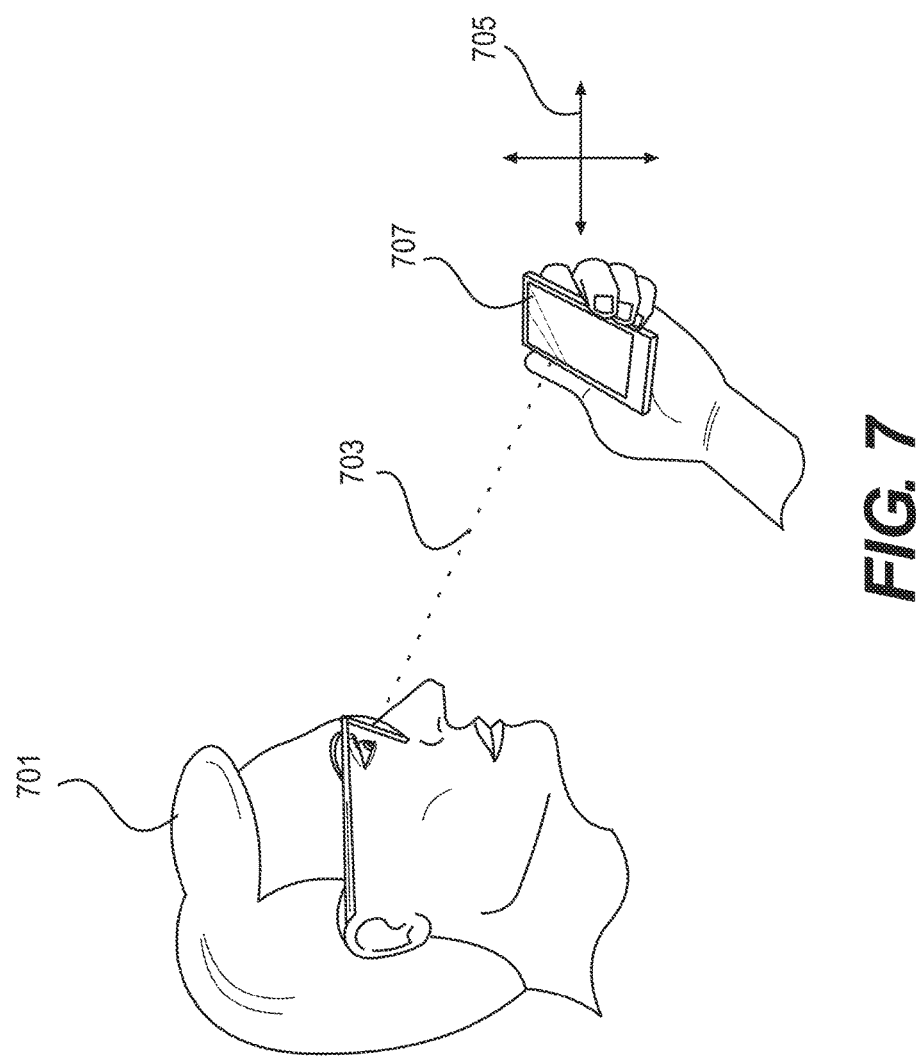
FIG. 7 includes a visual depiction of an assessment of a user's viewing habits, according to an embodiment of the present disclosure.

FIG. 7 includes a visual depiction of an assessment of a user's viewing habits (e.g., performed by assessment module 607), according to an embodiment of the present disclosure. In one embodiment, the assessment may include a computer system (e.g., of assessment module 607) obtaining measurement data 701 regarding a user's near and far binocular or monocular pupillary distance and preferred close reading distance 703 at a position 705. The close reading distance 703 may include a line of sight distance (e.g., from a user's pupils to a display on device 707 (taking into account an orientation (e.g., tilt, angle, yaw, or pitch) of the display and/or device 707 in space or relative to the user's anatomy)). Close reading distance 703 may further include x' or y' components of distance, e.g., an angle downwards at which the pupils are directed, relative to device 707. The assessment may be performed based on the user responding to a display on device 707. In some embodiments, device 707 may further function as an imaging device.

Figure 8:
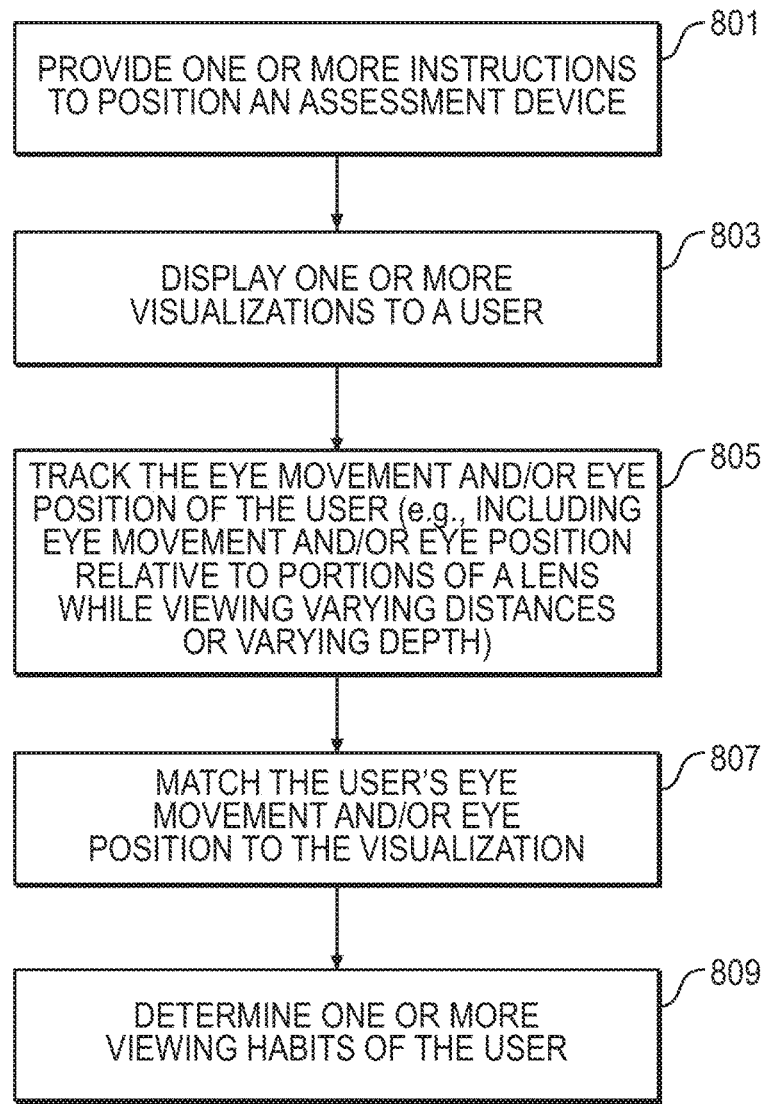
FIG. 8 depicts a flowchart of an exemplary method of assessing a user's viewing habits for optical measurements, according to an embodiment of the present disclosure.

FIG. 8 depicts a flowchart of an exemplary method 800 of assessing a user's viewing habits for optical measurements, according to an embodiment of the present disclosure. In one embodiment, exemplary method 800 includes an assessment (e.g., prompts or visualizations) to gather optical information about a user. Method 800 may be performed, for example, by a processor on a mobile device (e.g., user mobile device 601 of FIG. 6). In one embodiment, step 801 may include generating and displaying instructions (e.g., to a user) to hold and position an assessment device (e.g., the user's mobile device) at a comfortable and normal reading distance and position relative to the user while reading the text on the display. In one embodiment, the user's mobile device may also be performing the assessment. For example, step 803 may include the mobile device displaying text to be read, an image, graphics or animation that remains static or moves around the screen, or other information that a user may focus on. In another example, the display (e.g., of step 803) may include displaying varying text sizes and prompting the user to select the text size that is easy to read. In one instance, step 803 also includes the mobile device prompting the user to capture the user's response to the assessment. For example, step 803 may include prompting the user to audibly respond to a visualization and/or record the audible response during an assessment or at the end of the assessment (or steps of the assessment). Additionally, the user could press a button, tap an icon, slowly blink their eyes, etc. in response to the assessment or at the end of the assessment (or steps of the assessment). Alternately or in addition, step 803 may include prompting the user to focus on text or an image displayed on the screen (or on the image capture device directly), and then asking the user to focus on an object far in the distance. In some embodiments, capturing the user's response may be automated (e.g., automatically performed by the user's mobile device during the assessment) and/or performed by one or more other devices.

In another embodiment, the object to be held by the user at a comfortable reading distance and location may be a static object with printed text or graphics (e.g., a book or other text). The system, e.g., using a series of image capture devices or sensors, may simultaneously track the position/orientation of the user, the position/orientation of the static object to be read, and the locations of the user's pupils and/or irises. The object to be held can also be a mobile device with interactive text or graphics displayed, but as before, the actual determining of the 3D locations of the user, pupils, and read object can be determined by static hardware that is independent of the object held by the user.

In another embodiment, the steps disclosed herein for visual assessment can be performed while the user wears a set of multi-focal, progressive, or reading glasses. In one embodiment, the user may indicate to the system that said glasses are present, though this detection can also be automated such that the user need not indicate their presence for an assessment system to detect their presence. Allowing the user to wear a set of corrective optics may allow them to correctly see and focus on the display/text at the comfortable reading distance, as the only reason they would perform such an assessment is if they require a magnification aid in the first place.

In one embodiment, step 805 may include tracking the user's eye movement. For example, as the user reads the text or follows the prompted instructions, the mobile device may activate an imaging function that may capture image and/or depth data of the user with one or more cameras and/or depth sensors that may be in a known position relative to the displayed or highlighted text or displayed image. By tracking the user's eyes as they perform the assessment (or steps of the assessment), step 805 may include determining if a task is complete, as well as determining if the user performed the task correctly. For example, if the display showed the user a dot on the screen moving left-to-right and asked the user to track it with his eyes, step 805 may include tracking the motion of the eyes, triangulating where the eyes are focused, and determining if the eyes converged and tracked in the expected location on the display and/or moved in the expected direction (left-to-right).

Another embodiment may include prompting the user to stare directly into the imaging capture device when it is held at a comfortable reading distance and location, and solving for location/orientation of the imaging capture device with respect to the user, as well as the monocular near pupillary distance.

An exemplary assessment may include a user may simply holding a book or other text to read, and an entirely separate image capture device tracking not only the position/orientation of the text (e.g., by tracking fiducials printed on the corner of the page, by tracking the shape of the page, etc.), but also the position/orientation of the user and the position/orientation of his or her pupils and/or irises.

In one embodiment, step 807 may include matching, e.g., via a computer system of the mobile device, captured user data to the precise position of text or image displayed at any given moment in time, corresponding to the user's tracked/captured data. For example, in a scenario where a user audibly reads displayed text of the assessment, step 807 may include receiving microphone input and determining which word (of the display) a user may be viewing/focusing on at a given moment in time. In one embodiment, step 809 may include using the matching between the captured user data and displayed data, along with the calculated reading distance, to determine viewing habits (and consequently, optical information) for the user. For example, step 809 may include using the calculated reading distance and matching between the captured user data and displayed data to determine the magnification needed for the user's reading power. Step 809 may further include solving, using the mobile device, the 3D position and tilt of the capturing device (e.g., user mobile device 601 or image capture device(s) 605) with respect to the user's position. In doing so, step 809 may include projecting a ray between each of the user's pupils (or irises) and the image capturing device (e.g., if the user was staring directly into the image capturing device), and/or a ray from the pupils to the text or object the user was instructed to focus on. The location of the intersection of these two rays with the lenses (positioned in the eyewear) may include the locations where the center of the reading section of the lenses should be positioned. In addition, the pantoscopic tilt of the frames (and thereby the lenses held in the frames) can also be adjusted to achieve an optimum balance between the best optical properties when the user is focused straight-ahead on an object far in the distance, and when the user is focused on an object at a comfortable reading distance/location.

Moreover, the pantoscopic tilt may be an important input variable to the digitally-compensated lens algorithms, so that the resultant lens may minimize optical distortion(s) that may result in said positioning of the lens in front of the eye. For example, by adjusting the pantoscopic tilt of the frame (and thereby the lens), the lens algorithms need not work as hard to compensate for the tilt of the lens at extreme locations on the lens. Furthermore, with the advent of variable-base-curve progressive lenses, the ideal pantoscopic tilt at any given position of the lens can be more assuredly achieved by optimizing across, e.g., the tilt of the frame, the compensation within the digital lens design, and/or the additional tilt introduced due to the variable (increasing) base curve of the lens as you move down towards the reading section of said lens. By allowing the user to hold an imaging device (or object that is tracked by an external imaging device) at the position they find most comfortable, the system or assessment may also account for any left/right bias the user prefers when it comes to location of the ideal reading location. If the user's ideal reading location is biased 6 inches to their right (perhaps due to a right eye that is more dominant than the left eye), such a system may correctly calculate said location, calculate the rays that pass from the user's pupils to the reading target, calculate their intersection with the lens, and determine the correct reading locations for the left and right lens (and a bias of 6 inches to the right would correspond to a proportional shift to the right of 1-2 mm of the center of the reading section in both the left and right eye).

Step 809 may further include analyzing the user's response to prompts asking the user to focus on text or an image displayed on the screen, and then asking the user to focus on an object far in the distance, wherein the recorded image/depth data of the user's response may be used to compare near monocular or binocular $P_d$ to distance monocular/binocular $P_d$. As previously disclosed, the user's 3D anatomic model may include the monocular distance $P_d$ as a labeled vertex of the mesh. If the mesh is scaled appropriately, comparing the distance $P_d$ to near $P_d$ may provide a scaled measurement of near $P_d$.

Figure 9:
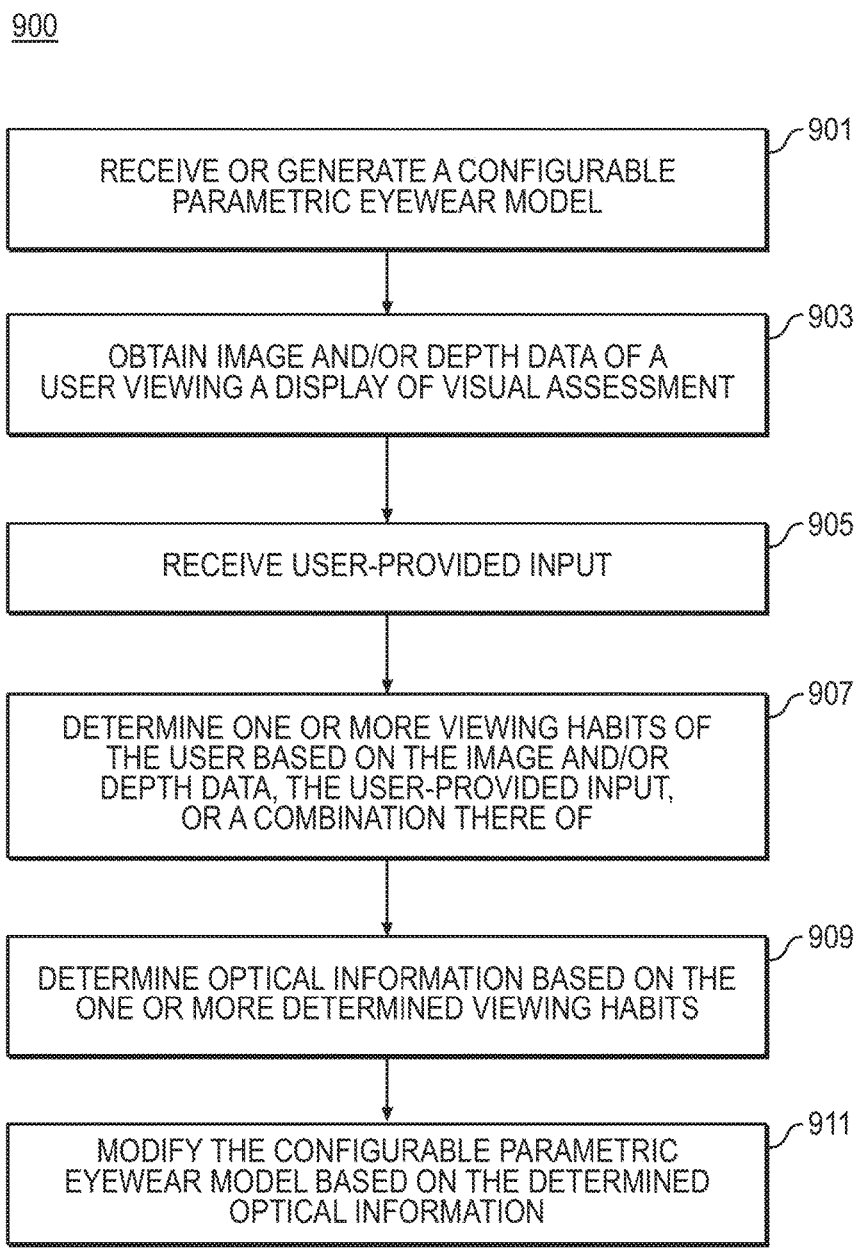
FIG. 9 depicts a flowchart of an exemplary method of customizing an eyewear product based on the gathered optical information, according to an embodiment of the present disclosure.

FIG. 9 depicts a flowchart of an exemplary method 900 of customizing an eyewear product based on the gathered optical information, according to an embodiment of the present disclosure. For example, method 900 may include a method of adjusting the parametric eyewear model and adjusting lens parameters (e.g., of the parametric model), for example, method 900 may include analyzing an anatomic model of a user and adjusting a configurable parametric model of an eyewear product to fit the user's anatomy and viewing habits. In one scenario, method 900 may include optimizing the parametric eyewear model to fit with the user's anatomy. The method may include calculating modifications to at least one parameter and updating the parametric model. Detailed descriptions of how parametric models may be optimized and adapted are described in U.S. patent application Ser. No. 14/466,619, filed Aug. 22, 2014, which is incorporated herein by reference in its entirety. In one embodiment, method 900 may be performed by a computer system, e.g., a computer system of user mobile device 601 in FIG. 6.

In one embodiment, step 901 may include receiving and/or generating a configurable parametric eyewear model. The configurable parametric eyewear model may include information regarding the user's anatomy and facial features, the precise dimensions, size, and shape of the parametric eyewear model, the spatial relationship between the eyewear model and the anatomic model, etc.

In one embodiment, step 903 may include obtaining, e.g., by a computer system, and image and/or depth data of the user viewing the display (e.g., of step 903 of method 800.) For example, the image and/or depth data may be captured while a user is reading text or graphics on a display, or staring directly at the display (or imaging device) or off at an object in the distance. Additionally, step 903 may include receiving additional information regarding the position and orientation of the capturing device providing the image and/or depth data. For example, the capturing device may be equipped with sensors, e.g., gyroscopes, accelerometers, barometers, depth sensors, depth provided by multi-camera sensors, etc. Step 903 may include the computer system receiving position or orientation information from the capturing device. The image or depth data may be captured in multiple images or multiple positions of the user or multiple images of the user reading such that their eyes move about the screen or static text in different positions. These multiple images may be analyzed by the computer system to either reduce error of any one measurement or to perform measurements in three dimensions by using multiple images to triangulate the positions that are measured. Additionally, a depth sensor may already provide 3D data that may be intrinsically scaled. Additionally, the computer system may use multiple images of the user's eye reading text to determine a region of optimal viewing position versus a single location that may be obtained from a single image.

In one embodiment, step 905 may include receiving user-provided input, e.g., the smallest size of text the user can read without any optical aid (progressive lenses or reading lenses)—this input may be used to determine the amount of magnification power the user requires. As previously disclosed, methods can be used to allow the system to know if the user is correctly performing a visual assessment, as well as determining when said assessment is complete. The user may indicate to the system that they are wearing corrective or magnified optics, though as also previously described the system may be able to automatically detect this and appropriately compensate for the correction/magnification.

In one embodiment, step 907 may include analyzing the user's viewing habits using the computer system. For example, step 907 may including determining the user's viewing habits by evaluating image data of the user reading text to determine the location of facial features and the alignment of an anatomic model of the user to the captured user image data. For example, the computer system may determine the location of the face, the location of specific facial features (including but not limited to the eyes, nose, pupils, eye corners, ears, etc.), and optimize camera parameters to align the anatomic face model with the detected facial features in the captured image data and/or depth data. The spatial position and orientation of the eyewear model relative to the captured image data may be based on an alignment of the anatomic model with the image data and/or depth data. The computer system may analyze the image/depth data to determine the location of the eyes (e.g., pupils and/or irises) (FIG. 3, 305), which may be focusing (FIG. 3, 307) on the text that is being read by the user at the time of image acquisition. The computer system may use any of a variety of techniques to detect the pupils or irises. For example, the computer system may use a machine learning technique that is trained on a database of prior data to detect pupils in image data based on histograms of oriented gradients (HOG), scaled invariant feature transform (SIFT) features of user image(s), and/or via Hough Circle Transform(s). Once the pupils are detected, the computer system may associate the location of the pupils with the anatomic model and the eyewear model. The distance between the pupils, e.g., the near $P_d$, may be determined from the scale associated with the models. Additionally, the distances between the pupils, the camera, and text that was read on the display may be determined based on known and determined camera parameters and/or depth information.

In one embodiment, step 909 may include determining optical information for the optical parameters of the configurable parametric eyewear model (e.g., of step 901), based on the user's viewing habits (e.g., of step 907). For example, the computer system may determine the optimal location to position the close distance (e.g., reading) optics relative to the rest of the lens and/or frames of the configurable parametric eyewear model. For instance, by calculating rays between the pupils and the text location that was read (relative to the camera location), the computer system may estimate the line of vision for each eye. The intersection of the ray and the lens, as positioned in the frame relative to the anatomic model, may be calculated as well. This intersection may represent the ideal center of placement of the near-distance optics (either a region in a progressive lens or a bifocal or trifocal lens).

In one embodiment, step 911 may include modifying the configurable parametric eyewear model (e.g., of step 901) based on the determined optical information. For example, the frame of the parametric model may be updated to adjust the pantoscopic tilt of the lens in order to achieve the ideal optical placement and angle of the near-distance optics with respect to the ray (discussed for step 909). The size of the region for placement of near-distance optics, for example, may be determined based on the overall shape and size of the lens, the digital lens design, the location of the intersection, and/or the angle and position of the user's preferred reading position relative to the eyewear and anatomic models.

In one embodiment, once parameters for the lens are determined (e.g., the front and back surface contours, distance $P_d$, prescription, base curve (or variable base curve), vertex distance, pantoscopic tilt, reading distance, reading $P_d$, segment height, reading section position, etc.), the parameters may be transferred to an optical lab or equipment to produce a custom lens meeting the specification used for the specific frames and the user's anatomy. In an exemplary embodiment, the frame of the configurable parametric eyewear model may be adjusted to match the optically best position and orient a stock lens. In an exemplary embodiment, the frames and/or lenses may be rendered and previewed, as previously discussed.

In an alternate embodiment, the frame and lens design may be produced or optimized together. The optical parameters used to the design the lens may be known, e.g., the vertex distance (how near or far the lens is from the eye), pantoscopic tilt (the angle of the lenses relative to the eye, which is especially important for reading distances when a person looks down through the lens). One advantage of a custom and personalized frame design is the ability to optimize parameters to best suit the individual user. For example, if a user regularly reads while looking down at an extreme angle, he may benefit from having a higher pantoscopic tilt (which is a frame parameter), a reading region that is positioned lower on the lens, and lenses that are taller and positioned lower on the face. A frame could be customized to accommodate taller lenses, and the frame could be adjusted to be positioned lower on the user's face. Or, if a user's nose bridge is very low, she may have trouble seeing through the lenses at their desired reading position and distance because normal frames may position the optics too close to her face. This user's customized eyewear product may include a vertex distance optimized to place the lenses at an ideal distance.

As another example, for a user suffering from myopia, the higher the minus power of the lens, the lower (or flatter) the ideal base curve of the lens to be used. If one inserts a base 2 lens (which may be very flat) in a frame that is designed for a base 6 lens (usual plano (non-Rx) lens that may have much more curvature), the lens may flatten out the frame and the temples may splay out, causing distance 229 in FIG. 2B to grow far too large to wear (and possibly far too large to manually adjust (heat and bend) the frame to fit). Conversely, if a base 6 lens is inserted in a frame designed for base 2, the temples may splay in and distance 229 in FIG. 2B may be far too small. Moreover, the curvature of the frame may fight the curvature of the lens that is inserted, which may cause the lens to pop out of the frame or cause premature failure of the material(s) (e.g., the lens and/or frame can crack). In the systems and methods described herein, however, for a given user's prescription, there may be an ideal base curve of the suitable lens. The parametric frame model can be adjusted such that it may be manufactured with the correct curvature to match the lens, and the temple length and temple splay angles can be adjusted with the values specific to that base curve.

In another embodiment, the parametric frame model can have its lens openings manufactured with an internal draft angle that matches the edged surface of any prescription lens (e.g., including those edged on a non-5-axis edging machine). This may allow the lens to be inserted in the frame without a mismatch that may cause in unwanted splay of the temples. On some 5-axis lens edging machines, the surface of the edge of the lens may be milled to be perpendicular to the front surface of the lens. As the base curve of the lens increases, so too may the angle of the lens edge (e.g., the sides of the cut lens). However, less-expensive some edging machines may mill or grind the edge of the lens parallel to the optical axis of the lens (or at a fixed angle). Therefore, the higher the base curve, the greater the mismatch may be between the lens edge surface and the corresponding edge in in the lens hole in the frames. By updating the parametric model to have its internal lens holes manufactured with angles that match those of an edged lens, the lens may fit correctly and the temples may remain undistorted.

In one embodiment, step 911 may further include optimizing the configurable parametric model. The inputs to optimizing the personalized frame and lens designs may concurrently include: the user's anatomic model, the parametric eyewear model, and the image data (or depth data) of the user reading or looking at the display of the computer system, and other sensor data from the imaging device (gyro, accelerometer, etc). The process for analyzing the image data to determine the pupil locations, alignment of the anatomic model, and the direction of vision while reading may be the same as previously described. The difference may lie in how the eyewear and lens models may be adapted.

An exemplary embodiment of optimization may include establishing a cost function for the various parameters of interest in the eyewear and lens designs. The parameters may include but are not limited to: the contour and size of the lens, lens base curve, vertex distance, pantoscopic tilt, reading section position, reading section size, the position of the eyewear on the nose, lens edging parameters, etc. By running such an optimization, one can achieve an output or outputs that achieve the best desired output, which can be a weighted balance of aesthetics, comfort, fit on the face, fit of the lens in the frame, optical acuity for distance viewing, optical acuity for reading, etc.

Other frame parameters that are not directly related or are influenced by the optical parameters may be optimized as well. An optimization function known to those familiar with the art, e.g., least squares, may be employed to set the parameters for the eyewear and lens models. Alternatively, some implementations may solve the parameters analytically without optimization if they can be directly solved.

Alternatively, the previously mentioned system and method may be applied with default, non-parametric eyewear. In this embodiment, the eyewear frame may not be adapted to the user and only the lens parameters may be adjusted. This may enable automatic and accurate fitting of multi-focal or progressive lenses to any traditional off-the-shelf frame for an individual.

In another embodiment, all the methods and techniques described herein are applied to the customization, rendering, display, and manufacture of custom eyewear cases. A user could select from a plurality of materials, colors, designs, shapes, and features and see an accurate rendering of the case on his display. Moreover, the case can automatically be sized to fit the custom eyewear designed such that the case securely contains the eyewear. For example, the case can be automatically designed to custom fit the eyewear such that it minimizes the size of the case and increases the case's ability to protect the eyewear in transport. The case color, style, and materials, and method of manufacture can also be matched to those used to make the custom eyewear. Custom text, e.g., the name of the user, may be engraved or marked on or in the case. The same eyewear manufacturing techniques described herein may also be used to manufacture the custom cases.

Those skilled in the art will recognize that the systems and methods described herein may also be used in the customization, rendering, display, and manufacture of other custom products. Since the technology described applies to the use of custom image data, anatomic models, and product models that are built for customization, a multitude of other products is designed in a similar way, for example: custom jewelry (e.g. bracelets, necklaces, earrings, rings, nose-rings, nose studs, tongue rings/studs, etc.), custom watches (e.g., watch faces, bands, etc.), custom cufflinks, custom bow ties and regular ties, custom tie clips, custom hats, custom bras, Inserts (pads), and other undergarments, custom swimsuits, custom clothing (jackets, pants, shirts, dresses, etc.), custom baby bottle tips and pacifiers (based on scan and reproduction of mother's anatomy), custom prosthetics, custom helmets (motorcycle, bicycle, ski, snowboard, racing, F1, etc.), custom earplugs (active or passive hearing protection), custom audio earphone (e.g., headphone) tips (over-the-ear and in-ear), custom Bluetooth headset tips (over-the-ear or in-ear), custom safety goggles or masks, and custom head-mounted displays.

It would also be apparent to one of skill in the relevant art that the present disclosure, as described herein, can be implemented in many different embodiments of software, hardware, firmware, and/or the entities illustrated in the figures. The operational behavior of embodiments may be described with the understanding that modifications and variations of the embodiments are possible, given the level of detail presented herein. It is to be understood that both the foregoing general description and the following detailed description are exemplary and explanatory only and are not restrictive of the disclosed embodiments, as claimed.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for generating a parametric model for the manufacture of a user-specific eyewear product, using a computer system, the method comprising:
    receiving a configurable parametric model of a user-specific eyewear product comprising a frame portion and a lens portion, wherein geometric parameters of the configurable parametric model are based on geometric features of a user's anatomy and one or more manufacturing constraints;
    receiving media data of a user, the media data including the user's response to one or more visual cues;
    detecting, from the received media data, movement of the user's eyes independent from movement of the user's head;

determining, based on the detected movement of the user's eyes, optical information of the user;

determining, based on the determined optical information, one or more geometrical parameters for the frame portion or for the lens portion of the received configurable parametric model;

generating an updated configurable parametric model based on the determined geometrical parameters and the one or more manufacturing constraints; and generating manufacturing specifications based on the updated configurable parametric model.

2. The method of claim 1, further comprising:

determining a visual cue of a display;

determining an association between the visual cue and the detected movement of the user's eyes; and determining a viewing habit of the user, the viewing habit including a user's eye movement relative to a lens.

3. The method of claim 1, wherein the optical information includes one or more of prescription information, lens type, lens thickness, lens curvature, lens size, optical design parameters, interpupilary distance, vertex distance, frame wrap, pantoscopic tilt, eyewear and frame outline, corrective needs of the user, the user's viewing habits, or a combination thereof.

4. The method of claim 1, further comprising:

determining a modification to the frame portion of the configurable parametric model in response to a modification to the lens portion of the configurable parametric model, or determining a modification to the lens portion of the configurable parametric model in response to a modification to the frame portion of the configurable parametric model.

5. The method of claim 4, wherein the modification to the lens portion of the configurable parametric model or the modification to the frame portion of the configurable parametric model includes a modification to a geometry of the lens portion of the configurable parametric model or a modification to a geometry of the frame portion of the configurable parametric model.

6. The method of claim 4, further comprising:

determining one or more geometric constraints, material constraints, or optical constraints of the configurable parametric model, wherein the modification to the lens portion of the configurable parametric model or the modification to the frame portion of the configurable parametric model is based on the one or more geometric constraints.

7. The method of claim 1, further comprising:

prompting production of a physical rendering of the user-specific eyewear product based on the updated configurable parametric model.

8. The method of claim 1, further comprising:

generating and displaying, to the user, a preview including the updated configurable parametric model and/or a simulation of a view through a lens of the updated configurable parametric model.

9. A system for generating a parametric model for the manufacture of a user-specific eyewear product, the system comprising:

a data storage device storing instructions for generating a parametric model for the manufacture of a user-specific eyewear product; and a processor configured to execute the instructions to perform a method including:

receiving a configurable parametric model of a user-specific eyewear product comprising a frame portion and a lens portion, wherein geometric parameters of the configurable parametric model are based on geometric features of a user's anatomy and one or more manufacturing constraints;

receiving media data of a user, the media data including the user's response to one or more visual cues;

detecting, from the received media data, movement of the user's eyes independent from movement of the user's head;

determining, based on the detected movement of the user's eyes, optical information of the user;

determining, based on the determined optical information, one or more geometrical parameters for the frame portion or for the lens portion of the received configurable parametric model;

generating an updated configurable parametric model based on the determined geometrical parameters and the one or more manufacturing constraints; and generating manufacturing specifications based on the updated configurable parametric model.

10. The system of claim 9, wherein the system is further configured for:

determining a visual cue of a display;

determining an association between the visual cue and the detected movement of the user's eyes; and determining a viewing habit of the user, the viewing habit including a user's eye movement relative to a lens.

11. The system of claim 9, wherein the optical information includes one or more of prescription information, lens type, lens thickness, lens curvature, lens size, optical design parameters, interpupilary distance, vertex distance, frame wrap, pantoscopic tilt, eyewear and frame outline, corrective needs of the user, the user's viewing habits, or a combination thereof.

12. The system of claim 11, wherein the system is further configured for:

determining a modification to the frame portion of the configurable parametric model in response to a modification to the lens portion of the configurable parametric model, or determining a modification to the lens portion of the configurable parametric model in response to a modification to the frame portion of the configurable parametric model.

13. The system of claim 11, wherein the modification to the lens portion of the configurable parametric model or the modification to the frame portion of the configurable parametric model includes a modification to a geometry of the lens portion of the configurable parametric model or a modification to a geometry of the frame portion of the configurable parametric model.

14. The system of claim 9, wherein the system is further configured for:

determining one or more geometric constraints, material constraints, or optical constraints of the configurable parametric model, wherein the modification to the lens portion of the configurable parametric model or the modification to the frame portion of the configurable parametric model is based on the one or more geometric constraints.

15. The system of claim 9, wherein the system is further configured for:

prompting production of a physical rendering of the user-specific eyewear product based on the updated configurable parametric model.

16. The system of claim 9, wherein the system is further configured for:

generating and displaying, to the user, a preview including the updated configurable parametric model and/or a simulation of a view through a lens of the updated configurable parametric model.

17. A non-transitory computer readable medium for use on a computer system containing computer-executable programming instructions for generating a parametric model for the manufacture of a user-specific eyewear product, the method comprising:
   receiving a configurable parametric model of a user-specific eyewear product comprising a frame portion and a lens portion, wherein geometric parameters of the configurable parametric model are based on geometric features of a user's anatomy and one or more manufacturing constraints;
   receiving media data of a user, the media data including the user's response to one or more visual cues;
   detecting, from the received media data, movement of the user's eyes independent from movement of the user's head;
   determining, based on the detected movement of the user's eyes, optical information of the user based on the detected movement of the user's eyes;
   determining, based on the determined optical information, one or more geometrical parameters for the frame portion or for the lens portion of the received configurable parametric model;
   generating an updated configurable parametric model based on the determined geometrical parameters and the one or more manufacturing constraints; and
   generating manufacturing specifications based on the updated configurable parametric model.

18. The non-transitory computer readable medium of claim 17, the method further comprising:
   determining a visual cue of a display;
   determining an association between the visual cue and the detected movement of the user's eyes; and
   determining a viewing habit of the user, the viewing habit including a user's eye movement relative to a lens.

19. The non-transitory computer readable medium of claim 17, wherein the optical information includes one or more of prescription information, lens type, lens thickness, lens curvature, lens size, optical design parameters, inter-pupilary distance, vertex distance, frame wrap, pantoscopic tilt, eyewear and frame outline, corrective needs of the user, the user's viewing habits, or a combination thereof.

20. The non-transitory computer readable medium of claim 19, the method further comprising:
   determining a modification to the frame portion of the configurable parametric model in response to a modification to the lens portion of the configurable parametric model, or determining a modification to the lens portion of the configurable parametric model in response to a modification to the frame portion of the configurable parametric model.

* * * * *